(12) United States Patent
Presta et al.

(10) Patent No.: US 8,580,938 B2
(45) Date of Patent: Nov. 12, 2013

(54) ENGINEERED ANTI-TSLP ANTIBODY

(75) Inventors: Leonard G. Presta, San Francisco, CA (US); Rene de Waal Malefyt, Sunnyvale, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/532,131

(22) Filed: Jun. 25, 2012

(65) Prior Publication Data

US 2013/0004508 A1    Jan. 3, 2013

Related U.S. Application Data

(63) Continuation of application No. 12/515,915, filed as application No. PCT/US2007/025531 on Dec. 13, 2007, now Pat. No. 8,232,372.

(60) Provisional application No. 60/869,974, filed on Dec. 14, 2006.

(51) Int. Cl.
*C07H 21/00* (2006.01)

(52) U.S. Cl.
USPC ................................................... 536/23.53

(58) Field of Classification Search
None
See application file for complete search history.

(56) References Cited

U.S. PATENT DOCUMENTS

| | | | |
|---|---|---|---|
| 6,555,520 B2 | 4/2003 | Sims et al. |
| 7,304,144 B2 | 12/2007 | Sims et al. |
| 7,405,058 B2 | 7/2008 | Sims et al. |
| 2005/0249712 A1 | 11/2005 | Leonard et al. |
| 2006/0171943 A1 | 8/2006 | Comeau et al. |
| 2006/0198822 A1 | 9/2006 | Booth et al. |

FOREIGN PATENT DOCUMENTS

| | | |
|---|---|---|
| EP | 1593690 | 11/2005 |
| EP | 1129190 | 5/2007 |
| JP | 2008109915 | 5/2008 |
| WO | WO92/11018 | 7/1992 |
| WO | WO00/39149 | 7/2000 |
| WO | WO03/032898 | 4/2003 |
| WO | WO03/065985 | 8/2003 |
| WO | WO2006/023791 | 3/2006 |
| WO | WO2007/045996 | 4/2007 |
| WO | WO2007/096149 | 8/2007 |
| WO | WO2008/012645 | 1/2008 |
| WO | WO2008/066444 | 6/2008 |
| WO | WO2009/035577 | 3/2009 |

OTHER PUBLICATIONS

Davies J. et al.: "Affinity Improvement of Single Antibody VH Domains: Residues in All Three Hypervariable Regions Affect Antigen Binding," Immunotechnology, Elsevier Science Publishers BV, NL, vol. 2, No. 3, Sep. 1996, pp. 169-179.

Holt L. J. et al."Domain Antibodies: Proteins for Therapy," Trends in Biotechnology, Elsevier Publications, Cambridge, GB, vol. 21, No. 11, Nov. 2003, pp. 484-490.

Online: "Anti-Human TSLP Antibody AF1398," Internet Citation, Feb. 15, 2006, Retrieved from the Internet: URL: http://www.rndsystems.com/pdf/af1398.pdf.

Online: "Monoclonal Anti-Human TSLP Antibody," Internet Citation, Aug. 6, 2005, Retrieved from the Internet: URL: http://www.rndsystems.com/pdf/MAB1398.pdf.

Soumelis V. et al: "Human Epithelial Cells Trigger Dendritic Cell Mediated Allergic Inflammation by Producing TSLP," Nature Immunology, Nature Publishing Group, GB, vol. 3. No. 7 Jul. 2002, pp. 673-680.

Soumelis V. et al.: "Human Thymic Stromal Lymphopoientin: A Novel Epithelial Cell-Derived Cytokine and A Potential Key Player in the Induction of Allergic Inflammation," Springer Seminar in Immunopathology, Springer Verlag, DE, vol. 25, No. 3-4, Feb. 2004, pp. 325-333.

International Search Report for PCT/US2007/025531, 5 pages.

Fundamental Immunology, p. 242, William E. Paul, M.D. ed., 3d ed; 1993.

*Primary Examiner* — Brad Duffy

(74) *Attorney, Agent, or Firm* — Patricia L. Chisholm; Immac J. Thampoe

(57) ABSTRACT

The invention relates to binding compounds that specifically bind to human TSLP, as well as uses thereof, e.g., in the treatment of inflammatory disorders.

6 Claims, No Drawings

ENGINEERED ANTI-TSLP ANTIBODY

CROSS REFERENCE TO RELATED APPLICATIONS

This application is a continuation of U.S. application Ser. No. 12/515,915, filed Sep. 17, 2009 now U.S. Pat. No. 8,232,372, which is the national stage filing under 35 U.S.C. §371 of International Patent Application No. PCT/US2007/025531, filed Dec. 13, 2007, which claims the benefit of U.S. Provisional Application Ser. No. 60/869,974, filed Dec. 14, 2006; the disclosures of which are incorporated herein by reference in their entireties.

REFERENCE TO SEQUENCE LISTING SUBMITTED ELECTRONICALLY

The sequence listing of the present application is submitted electronically via EFS-Web as an ASCII formatted sequence listing with a file name "BP06556SeqListing_ST25.txt" creation date of Mar. 3, 2010 and a size of 20.9 KB. This sequence listing submitted via EFS-Web is part of the specification and is herein incorporated by reference in its entirely.

FIELD OF THE INVENTION

The present invention relates generally to a thymic stromal lymphopoietin (TSLP) specific antibody, and uses thereof, particularly in inflammatory, and allergic inflammatory disorders.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. An immune response can produce pathological consequences, e.g., when it involves excessive inflammation, as in allergic inflammatory disorders.

TSLP is an immune cytokine that induces dendritic cell-mediated $CD4^+$ T cell responses with a proallogenic phenotype (Gilliet et al., *J. Exp. Medicine* 197(8): 1059-1063 (2003). TSLP is involved in the initiation of allergic inflammation (Watanabe et al., *Nature Immunology* 5: 426-434 (2004); Soumelis et al., *Nature Immunology* 3: 673-680 (2002)).

Antibodies are being developed against a number of antigen targets that are involved in immune diseases. The most significant limitation in using antibodies as a therapeutic agent in vivo is the immunogenicity of the antibodies. As most monoclonal antibodies are derived from rodents, repeated use in humans results in the generation of an immune response against the therapeutic antibody. Such an immune response results in a loss of therapeutic efficacy at a minimum and a potential fatal anaphylactic response at a maximum. Initial efforts to reduce the immunogenicity of rodent antibodies involved the production of chimeric antibodies, in which mouse variable regions were fused with human constant regions. Liu et al. (1987) *Proc. Natl. Acad. Sci. USA* 84:3439-43. However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

It is generally believed that complementarity determining region (CDR) loops of variable domains comprise the binding site of antibody molecules. Therefore, the grafting of rodent CDR loops onto human frameworks (i.e., humanization) was attempted to further minimize rodent sequences. Jones et al. (1986) *Nature* 321:522; Verhoeyen et al. (1988) *Science* 239: 1534. However, CDR loop exchanges may not uniformly result in an antibody with the same binding properties as the antibody of origin. Changes in framework residues (FR), residues involved in CDR loop support, in humanized antibodies may also be required to preserve antigen binding affinity. Kabat et al. (1991) *J. Immunol.* 147:1709. While the use of CDR grafting and framework residue preservation in a number of humanized antibody constructs has been reported, it is difficult to predict if a particular sequence will result in the antibody with the desired binding, and sometimes biological, properties. See, e.g., Queen et al. (1989) *Proc. Natl. Acad. Sci. USA* 86:10029, Gorman et al. (1991) *Proc. Natl. Acad. Sci. USA* 88:4181, and Hodgson (1991) *Biotechnology (NY)* 9:421-5.

The present invention provides an engineered TSLP antibody and uses thereof to treat inflammatory, and particularly allergic inflammatory, disorders.

SUMMARY OF THE INVENTION

The present invention provides a binding compound that specifically binds human and cyno TSLP, comprising: at least one antibody heavy chain variable region, or a TSLP-binding fragment thereof, said heavy chain variable region comprising at least one CDR sequence selected from the group consisting of SEQ ID NOs: 1, 2 and 3; or at least one antibody light chain variable region, or a TSLP-binding fragment thereof, said light chain variable region comprising at least one CDR sequence selected from the group consisting of SEQ ID NOs: 4, 5 and 6.

The present invention also provides a binding compound that specifically binds to human and cyno TSLP comprising at least one antibody heavy chain variable region, or a TSLP-binding fragment thereof, said heavy chain variable region comprising at least one CDR sequence selected from the group consisting of SEQ ID NOs: 1, 2 and 3; and at least one antibody light chain variable region, or a TSLP-binding fragment thereof, said light chain variable region comprising at least one CDR sequence selected from the group consisting of SEQ ID NOs: 4, 5 and 6.

In some embodiments, the antibody heavy chain variable region, or TSLP-binding fragment thereof, comprises at least two CDR sequences selected from the group consisting of SEQ ID NOs: 1, 2 and 3. In other embodiments, the antibody heavy chain variable region, or TSLP-binding fragment thereof, has the three CDR sequences set forth in SEQ ID NOs: 1, 2 and 3;.

In some embodiments, the antibody light chain variable region, or TSLP-binding fragment thereof, comprises at least two CDR sequences selected from the group consisting of SEQ ID NOs: 4, 5 and 6. In other embodiments, the antibody light chain variable region, or TSLP-binding fragment thereof, has the three CDR sequences set forth in SEQ ID NOs: 4, 5 and 6.

The present invention also provides a binding compound that specifically binds human and cyno TSLP, comprising: at least one antibody heavy chain variable region, or a TSLP-binding fragment thereof, said heavy chain variable region comprising: the CDR-H1 of SEQ ID NO. 1, or a variant thereof; the CDR-H2 of SEQ ID NO. 2, or a variant thereof; and the CDR-H3 of SEQ ID NO. 3, or a variant thereof; or at least one antibody light chain variable region, or a TSLP-binding fragment thereof, said light chain variable region comprising: the CDR-L1 of SEQ ID NO. 4, or a variant thereof; the CDR-L2 of SEQ ID NO. 5, or a variant thereof; and the CDR-L3 of SEQ ID NO. 6, or a variant thereof. The present invention also provides a binding compound that specifically binds human and cyno TSLP, comprising at least one antibody heavy chain variable region, or a TSLP-binding fragment thereof, said heavy chain variable region comprising: the CDR-H1 of SEQ ID NO. 1, or a variant thereof; the CDR-H2 of SEQ ID NO. 2, or a variant thereof; and the CDR-H3 of SEQ ID NO. 3, or a variant thereof; and at least one antibody light chain variable region, or a TSLP-binding fragment thereof, said light chain variable region comprising: the CDR-L1 of SEQ ID NO. 4, or a variant thereof; the CDR-L2 of SEQ ID NO. 5, or a variant thereof; and the CDR-L3 of SEQ ID NO. 6, or a variant thereof. In one embodiment, the variant comprises up to 20 conservatively modified amino acid residues. In one embodiment, the variant comprises up to 10 conservatively modified amino acid residues. In one embodiment, the variant comprises up to 5 conservatively modified amino acid residues. In one embodiment, the variant comprises up to 3 conservatively modified amino acid residues.

In some embodiments of the above described binding compounds, all or substantially all of the remainder of the heavy chain variable region is all or substantially all a human Ig region; and all or substantially all of the remainder of the light chain variable region variable region is all or substantially all a human Ig region. In preferred embodiments, the remainder of the heavy chain variable region is human heavy chain amino acid sequence; and the remainder of the light chain variable region is human light chain amino acid sequence.

The present invention also provides a binding compound that specifically binds human and cyno TSLP, comprising: a heavy chain variable region comprising residues 1-116 of SEQ ID NO: 10 or a variant thereof; and a light chain variable region comprising residues 1-108 of SEQ ID NO: 12, or a variant thereof. In one embodiment, the variant comprises up to 20 conservatively modified amino acid residues. In one embodiment, the variant comprises up to 10 conservatively modified amino acid residues. In one embodiment, the variant comprises up to 5 conservatively modified amino acid residues. In one embodiment, the variant comprises up to 3 conservatively modified amino acid residues. In one embodiment, the light chain variable region comprises a variant wherein the amino acid at position 49 of SEQ ID NO:12 has been changed from Y to K.

The present invention also provides a binding compound that specifically binds human and cyno TSLP, comprising: a heavy chain variable region comprising residues 1-116 of SEQ ID NO: 10; and a light chain variable region comprising residues 1-108 of SEQ ID NO: 12.

The present invention also provides a binding compound that specifically binds human and cyno TSLP, comprising: a heavy chain variable region consisting essentially of residues 1-116 of SEQ ID NO: 10; and a light chain variable region consisting essentially of residues 1-108 of SEQ ID NO: 12.

The present invention also provides a binding compound that specifically binds human and cyno TSLP, comprising: a heavy chain variable region having at least 95%, 90%, 85% or 80% homology to residues 1-116 of SEQ ID NO: 10; and/or a light chain variable region having at least 95%, 90%, 85% or 80% homology to residues 1-108 of SEQ ID NO: 12. In one embodiment, the invention provides a binding compound that specifically binds human and cyno TSLP, comprising: a heavy chain variable region having at least 90% homology to residues 1-116 of SEQ ID NO: 10; and a light chain variable region having at least 90% homology to residues 1-108 of SEQ ID NO: 12. In some embodiments, the heavy chain variable region will comprise at least 95% homology to residues 1-116 of SEQ ID NO: 10; and the light chain variable region will comprise at least 95% homology to residues 1-108 of SEQ ID NO: 12.

In some embodiments, the binding compounds of the invention also comprise a heavy chain constant region and/or a light chain constant region. In one embodiment, the heavy chain constant region comprises a $\gamma 1$, $\gamma 2$, $\gamma 3$, or $\gamma 4$ human heavy chain constant region or a variant thereof. In various embodiments the light chain constant region comprises a lambda or a kappa human light chain constant region.

In some embodiments, the binding compound of the invention is an antibody or an antigen binding fragment thereof. In various embodiments the antibody or fragment thereof of the present invention is polyclonal, monoclonal, chimeric, cynoized, humanized or fully human. In a preferred embodiment, the antibody is a humanized antibody or a fragment thereof.

The present invention also contemplates that the binding fragment is an antibody fragment selected from the group consisting of Fab, Fab', Fab'-SH, Fv, scFv, F(ab')$_2$, and a diabody. The present invention also contemplates that the binding compound is a nanobody, an avimer, or an aptimer.

In a preferred embodiment, the binding compound is the antibody produced by the hybridoma deposited as PTA-7951. In another embodiment, the binding compound is not the antibody produced by the hybridoma deposited as PTA-7951.

The invention also encompasses an antibody or antigen biding fragment thereof that specifically binds to human and cyno-TSLP comprising the heavy chain amino acid sequence of SEQ ID NO: 18, or a variant thereof; and/or a light chain amino acid sequence of SEQ ID NO:17 or a variant thereof. The invention also encompasses an antibody or antigen biding fragment thereof that specifically binds to human and cyno-TSLP comprising amino acids 19 to 472 of SEQ ID NO: 18, or a variant thereof; and/or amino acids 20 to 233 of SEQ ID NO:17 or a variant thereof. In one embodiment, the variant comprises up to 20 conservatively modified amino acid residues. In one embodiment, the variant comprises up to 10 conservatively modified amino acid residues. In one embodiment, the variant comprises up to 5 conservatively modified amino acid residues. In one embodiment, the variant comprises up to 3 conservatively modified amino acid residues.

The present invention also comprises a binding compound that specifically binds human and cyno TSLP, wherein said binding compound has a KD of about 2.1 pM or less, as measured using KinExA technology and human TSLP as the ligand. The present invention also comprises a binding compound that specifically binds human and cyno TSLP, wherein said binding compound has a KD of 2.1 pM (+/− two-fold), as measured using KinExA technology and human TSLP as the ligand. In one embodiment, the binding compound is a humanized anti-TSLP antibody or an antigen binding fragment thereof.

The present invention also comprises a binding compound that specifically binds human and cyno TSLP, wherein said binding compound has a KD of about 111 pM or less, as measured using surface plasmon resonance and human TSLP as the ligand. The present invention also comprises a binding compound that specifically binds human and cyno TSLP, wherein said binding compound has a KD of 111 pM (+/− two-fold), as measured using surface plasmon resonance and human TSLP as the ligand. In one embodiment, the binding compound is a humanized anti-TSLP antibody or an antigen binding fragment thereof.

The present invention also comprises a binding compound that specifically binds human and cyno TSLP, wherein said binding compound has an EC50 of about 7.6 nM or less. The present invention also comprises a binding compound that specifically binds human and cyno TSLP, wherein said binding compound has an EC50 of about 7.6 nM (+/− two-fold). (The EC50 refers to the concentration of binding compound required to neutralize human TSPL to 50% of the level observed in the absence of the binding compound.) In one embodiment, the binding compound is a humanized anti-TSLP antibody or an antigen binding fragment thereof.

The present invention also provides an isolated nucleic acid encoding at least one of the heavy chain variable region or light chain variable region of the binding compound of the invention. Also provided is an expression vector comprising the nucleic acid operably linked to control sequences that are recognized by a host cell when the host cell is transfected with the vector. Also provided are a host cell comprising the expression vector.

Also provided is a method of producing a polypeptide comprising a heavy chain variable region or a light chain variable region of the invention comprising: culturing the host cell of in culture medium under conditions wherein the nucleic acid sequence is expressed, thereby producing polypeptides comprising the light and heavy chain variable regions; and recovering the polypeptides from the host cell or culture medium.

The invention also provides a binding compound (for example an antibody or antigen binding fragment thereof) that specifically binds to the epitope on human TSLP that is bound by the antibody produced by the hybridoma deposited as PTA-7951, wherein the antibody that specifically binds to the epitope on human TSLP is not the antibody produced by the hybridoma deposited as PTA-7951.

The invention also comprises a binding compound (for example an antibody or antigen binding fragment thereof) that competitively inhibits binding by the antibody produced by the hybridoma deposited as PTA-7951 to human TSLP, wherein the antibody that competitively inhibits binding is not the antibody produced by the hybridoma deposited as PTA-7951.

The invention also comprises a binding compound (for example an antibody or antigen binding fragment thereof) that blocks TSLP-mediated activity. TSLP mediated activities include, but are not limited to, binding to its receptor, promoting the activation of dendritic cells leading to proliferation or survival of $T_H2$ cells, secretion of $T_H2$ attracting chemokines by dendritic cells such as TARC and MDC, production of pro-allergic cytokines such as IL-4, IL-5, IL-13 and TNF-alpha. A number of assays can be employed to determine whether a binding compound blocks TSLP-mediated activity. These include the assays described n the Examples and other assays, including those described in the art. See, e.g., Reche et al., *J. Immunol.* 167:336-43 (2001); Isaksen et al., *J. Immunol.* 168:3288-94 (2002).

In one embodiment, the binding compound is able to block the binding of TSLP to TSLPR in a cross-blocking assay.

The present invention encompasses a method of suppressing an immune response in a human subject comprising administering to a subject in need thereof an a binding compound that specifically binds human and cyno TSLP, in an amount effective to block the biological activity of TSLP. The present invention also contemplates administering an additional immunosuppressive or anti-inflammatory agent. In a preferred embodiment, the immune response is asthma. In another preferred embodiment, the immune response is allergic inflammation. In another preferred embodiment, the allergic inflammation is allergic rhinosinusitis, allergic asthma, allergic conjunctivitis, or atopic dermatitis. In another preferred embodiment, the immune response is fibrosis, inflammatory bowel disease or Hodgkin's lymphoma. In another preferred embodiment, the binding compound is administered in combination with another immunomodulatory agent.

The antibody or fragment thereof of the present invention can be in a composition comprising the binding compound of the invention, in combination with a pharmaceutically acceptable carrier or diluent. In a further embodiment, the composition further comprises an immunosuppressive or anti-inflammatory agent.

The present invention also encompasses a composition comprising a binding compound of the invention and a pharmaceutically acceptable carrier or diluent.

The present invention encompasses an isolated nucleic acid encoding the polypeptide sequence of the antibody or fragment thereof of the present invention. The nucleic acid can be in an expression vector operably linked to control sequences recognized by a host cell transfected with the vector. Also encompassed is a host cell comprising the vector, and a method of producing a polypeptide comprising culturing the host cell under conditions wherein the nucleic acid sequence is expressed, thereby producing the polypeptide, and recovering the polypeptide from the host cell or medium.

In various embodiments, the invention relates to medicaments comprising the antibody or fragment thereof of the present invention. For example, the invention encompasses the use of a binding compound that specifically binds human and cyno TSLP (for example, any one of the binding compounds according to the invention) for the preparation of a medicament to treat suppress an immune response. The present invention encompasses the use of a binding compound that specifically binds human and cyno TSLP (for example, any one of the binding compounds according to the invention) for the preparation of a medicament to treat asthma. The present invention encompasses the use of a binding compound that specifically binds human and cyno TSLP (for example, any one of the binding compounds according to the invention) for the preparation of a medicament to treat an inflammatory disorder. In one embodiment, the inflammatory disorder is an allergic inflammatory disorder. In one embodiment, the allergic inflammatory disorder is allergic rhinosinusitis, allergic asthma, allergic conjunctivitis, or atopic dermatitis.

DETAILED DESCRIPTION

As used herein, including the appended claims, the singular forms of words such as "a," "an," and "the," include their corresponding plural references unless the context clearly dictates otherwise. All references cited herein are incorporated by reference to the same extent as if each individual publication, patent application, or patent, was specifically and individually indicated to be incorporated by reference.

I. Definitions

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications.

As used herein, the term "antibody" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, the term "TSLP binding fragment" or "binding fragment thereof" encompasses a fragment or a derivative of an antibody that still substantially retain its biological activity of inhibiting TSLP activity. Therefore, the term "antibody fragment" or TSLP binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; domain antibodies; and multispecific antibodies formed from antibody fragments. Typically, a binding fragment or derivative retains at least 10% of its TSLP inhibitory activity. Preferably, a binding fragment or derivative retains at least 25%, 50%, 60%, 70%, 80%, 90%, 95%, 99% or 100% (or more) of its TSLP inhibitory activity, although any binding fragment with sufficient affinity to exert the desired biological effect will be useful. It is also intended that a TSLP binding fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al., (1991) Nature 352: 624-628 and Marks et al., (1991) J. Mol. Biol. 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984) Proc. Natl. Acad. Sci. USA 81: 6851-6855).

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079, which are hereby incorporated by reference in their entireties). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hu" or "hum" is added to antibody clone designations when necessary to distinguish humanized antibodies (e.g., "hu23B12") from parental rodent antibodies (e.g., rat 23B12, or "r23B12"). The humanized forms of rodent antibodies will generally comprise the same CDR sequences of the parental rodent antibodies, although certain amino acid substitutions may be included to increase affinity or increase stability of the humanized antibody.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al., (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing. See Tables 2 and 3, in which sequence numbering is with reference to the Sequence Listing.

"Binding" refers to an association of the binding composition with a target where the association results in reduction in the normal Brownian motion of the binding composition, in cases where the binding composition can be dissolved or suspended in solution.

"Binding compound" refers to a molecule that comprises one or more amino acid sequences that specifically bind to human TSLP. In one preferred embodiment, the binding compound is an antibody. In another preferred embodiment, the binding compound comprises an antibody fragment.

"Binding composition" refers to a TSLP-binding compound in combination with a stabilizer, excipient, salt, buffer, solvent, or additive, capable of binding to a target.

"Conservatively modified variants" or "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, The Benjamin/Cummings Pub. Co., p. 224 (4th Edition 1987)). Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The terms "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a nonlimiting example, an antibody or fragment thereof that consists essentially of a recited amino acid sequence may also include one or more amino acids, including substitutions of one or more amino acid residues, that do not materially affect the properties of the binding compound.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context.

"Endogenous" refers to substances that are produced within a cell, organism, or human body, depending on the context.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences. Any suitable source of unrearranged immunoglobulin DNA may be used.

"Inhibitors" are compounds that decrease, block, prevent, delay activation, inactivate, desensitize, or down regulate, e.g., a gene, protein, ligand, receptor, or cell. An inhibitor may also be defined as a composition that reduces, blocks, or inactivates a constitutive activity. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%.

Endpoints in inhibition can be monitored as follows. Inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Specifically" or "selectively" binds, when referring to a ligand/receptor, antibody/antigen, or other binding pair, indicates a binding reaction which is determinative of the presence of the protein, e.g., TSLP, in a heterogeneous population of proteins and/or other biologics. Thus, under designated conditions, a specified ligand/antigen binds to a particular receptor/antibody and does not bind in a significant amount to other proteins present in the sample.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis (Munsen, et al. (1980) *Analyt. Biochem.* 107:220-239).

As used herein, the term "inflammatory disorder" refers to any disease or disorder characterized by local inflammation at a site of injury or infection and includes, without limitation, allergic inflammation, autoimmune diseases, and other disorders characterized by undesired immune cell accumulation at a local tissue site.

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents," "immunosuppressive drugs," or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified into four groups: glucocorticoids cytostatics; antibodies (including Biological Response Modifiers or DMARDs); drugs acting on immunophilins; other drugs, including known chemotherpeutic agents used in the treatment of proliferative disorders. For multiple sclerosis, in particular, the antibodies of the present invention can be administered in conjunction with a new class of myelin binding protein-like therapeutics, known as copaxones.

"Anti-inflammatory agents" or "anti-inflammatory drugs", is used to represent both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: Systemic vasculitis (inflammation of blood vessels); and Myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs, and sulphonanilides.

II. General

The present invention provides engineered anti-TSLP antibodies and uses thereof to treat inflammatory, and particularly allergic inflammatory, disorders. In a preferred embodiment, the inflammatory disorder is asthma. In a preferred embodiment, the allergic inflammatory disorder is allergic rhinosinusitis, allergic asthma, allergic conjunctivitis, or atopic dermatitis. The present invention also provides engineered anti-TSLP antibodies to treat fibrosis, inflammatory bowel disease or Hodgkin's lymphoma.

TSLP is a member of the 'long chain' family of hematopoetic cytokines. Insights into the structural basis of 'long chain' cytokine/receptor recognition have shown that although large areas of protein surface are buried in formation of cytokine—receptor complexes, the affinity of the interaction is dominated by a few, often tightly clustered amino acid residues forming an energetic 'hot spot' in the center of the binding interface. The identity of the residues that dominate the binding energy of a large protein-protein interface has been termed the 'functional epitope'. The affinity of the interaction (and hence biological specificity) is consequently defined by the structural complementarity of the functional epitopes of ligand and receptor. Detailed mutagenesis studies have shown that the most significant residues that make up the functional epitopes of cytokines and receptors are hydrophobic contacts involving either non-polar side chains such as tryptophan, the aliphatic components of non-polar side chains or the polypeptide backbone. The non-polar 'core' is surrounded by a halo of polar residues of lesser importance for binding energy. Kinetic studies indicate that the primary role of the functional epitopes is to stabilize protein-protein interaction by decreasing the dissociation rate of the complex. It has been suggested that the initial contact between cytokine and receptor is dominated by random diffusion or 'rolling' of protein surfaces producing many unstable contacts. The complex is then stabilized when the functional epitopes of the receptor and ligand engage (see, e.g., Bravo and Heath, supra).

III. Generation of TSLP Specific Antibodies

Any suitable method for generating monoclonal antibodies may be used. For example, a recipient may be immunized with a linked or unlinked (e.g. naturally occurring) form of the TSLP heterodimer, or a fragment thereof. Any suitable method of immunization can be used. Such methods can include adjuvants, other immunostimulants, repeated booster immunizations, and the use of one or more immunization routes.

Any suitable source of TSLP can be used as the immunogen for the generation of the non-human antibody, of the compositions and methods disclosed herein. Such forms include, but are not limited to whole protein, including linked and naturally occurring heterodimers, peptide(s), and epitopes, generated through recombinant, synthetic, chemical or enzymatic degradation means known in the art.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Any suitable method can be used to elicit an antibody with the desired biologic properties to inhibit TSLP. It is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle, et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275-1281.

Other suitable techniques involve selection of libraries of antibodies in phage or similar vectors. See, e.g., Huse et al., Science 246:1275-1281 (1989); and Ward et al., Nature 341:544-546 (1989). The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) Proc. Nat'l Acad. Sci. USA 86:10029-10033; or made in transgenic mice, see Mendez et al. (1997) Nature Genetics 15:146-156; also see Abgenix and Medarex technologies.

Antibodies or binding compositions against predetermined fragments of TSLP can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective TSLP. These monoclonal antibodies will usually bind with at least a $K_d$ of about 1 µM, more usually at least about 300 nM, typically at least about 30 nM, preferably at least about 10 nM, more preferably at least about 3 nM or better, usually determined by ELISA.

IV. Humanization of TSLP Specific Antibodies

Any suitable non-human antibody can be used as a source for the hypervariable region. Sources for non-human antibodies include, but are not limited to, murine, Lagomorphs (including rabbits), bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance of the desired biological activity. For further details, see Jones et al. (1986) Nature 321:522-525; Reichmann et al. (1988) Nature 332:323-329; and Presta (1992) Curr. Op. Struct. Biol. 2:593-596.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. 438 310) and Winter (European Patent Application Publication No. 239400).

Amino acid sequence variants of humanized anti-TSLP antibody are prepared by introducing appropriate nucleotide changes into the humanized anti-TSLP antibody DNA, or by peptide synthesis. Such variants include, for example, deletions from, and/or insertions into and/or substitutions of, residues within the amino acid sequences shown for the humanized anti-TSLP F(ab). Any combination of deletion, insertion, and substitution is made to arrive at the final construct, provided that the final construct possesses the desired characteristics. The amino acid changes also may alter post-translational processes of the humanized anti-TSLP antibody, such as changing the number or position of glycosylation sites.

A useful method for identification of certain residues or regions of the humanized anti-TSLP antibody polypeptide that are preferred locations for mutagenesis is called "alanine scanning mutagenesis," as described by Cunningham and Wells (1989) *Science* 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with TSLP antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-TSLP antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-TSLP antibody with an N-terminal methionyl residue or the antibody fused to an epitope tag. Other insertional variants of the humanized anti-TSLP antibody molecule include the fusion to the N- or C-terminus of humanized anti-TSLP antibody of an enzyme or a polypeptide which increases the serum half-life of the antibody.

Another type of variant is an amino acid substitution variant. These variants have at least one amino acid residue in the humanized anti-TSLP antibody molecule removed and a different residue inserted in its place. The sites of greatest interest for substitutional mutagenesis include the hypervariable loops, but FR alterations are also contemplated. Hypervariable region residues or FR residues involved in antigen binding are generally substituted in a relatively conservative manner.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Yet another type of amino acid variant is the substitution of residues to provide for greater chemical stability of the final humanized antibody. For example, an asparagine (N) residue may be changed to reduce the potential for formation of isoaspartate at any NG sequences within a rodent CDR. In one embodiment, the asparagine is changed to glutamine (Q). Isoaspartate formation may debilitate or completely abrogate binding of an antibody to its target antigen. Presta (2005) *J. Allergy Clin. Immunol.* 116:731 at 734. In addition, methionine residues in rodent CDRs may be changed to reduce the possibility that the methionine sulfur would oxidize, which could reduce antigen binding affinity and also contribute to molecular heterogeneity in the final antibody preparation. Id. In one embodiment, the methionine is changed to alanine (A). Antibodies with such substitutions are subsequently screened to ensure that the substitutions do not decrease TSLP binding affinity to unacceptable levels.

Nucleic acid molecules encoding amino acid sequence variants of humanized TSLP specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-TSLP antibody.

Ordinarily, amino acid sequence variants of the humanized anti-TSLP antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95%. Identity or homology with respect to this sequence is defined herein as the percentage of amino acid residues in the candidate sequence that are identical with the humanized anti-TSLP residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described below.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal. Typically, at least 75% of the humanized antibody residues will correspond to those of the non-human CDR residues, more often 90%, and most preferably greater than 95%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%.

CDR and FR residues are determined according to the standard sequence definition of Kabat. Kabat et al., Sequences of Proteins of Immunological Interest, National Institutes of Health, Bethesda Md. (1987). Table 2 provides sequence identifier information for the rat (r23B12) and human (hu23B12) variable heavy chain CDRs. Table 3 provides sequence identifier information for the r23B12 and hu23B12 variable light chain CDRs.

TABLE 2

Heavy Chain Sequences and Domains

| ANTIBODY CLONE | SEQ ID NO: | $V_H$ RESIDUES | HEAVY CHAIN CDR RESIDUES | | |
|---|---|---|---|---|---|
| | | | CDR-H1 | CDR-H2 | CDR-H3 |
| r23B12 | 7 | 1-116 | 26-35 | 50-65 | 95-105 |
| hu23B12 | 10 | 1-116 | 26-35 | 50-65 | 95-105 |

TABLE 3

Light Chain Sequences and Domains

| ANTIBODY CLONE | SEQ ID NO: | $V_L$ RESIDUES | LIGHT CHAIN CDR RESIDUES | | |
|---|---|---|---|---|---|
| | | | CDR-L1 | CDR-L2 | CDR-L3 |
| r23B12 | 8 | 1-108 | 24-34 | 50-56 | 89-97 |
| hu23B12 | 12 | 1-108 | 24-34 | 50-56 | 89-97 |

The r23B12 and hu23B12 CDR-H1 sequence is GYIFTDYAMH (SEQ ID NO. 1). The r23B12 and hu23B12 CDR-H2 sequence is TFIPLLDTSDYNQNFKG (SEQ ID NO. 2). The r23B12 and hu23B12 CDR-H3 sequence is MGVTHSYVMDA (SEQ ID NO. 3).

The r23B12 and hu23B12 CDR-L1 sequence is RASQPISISVH (SEQ ID NO. 4). The r23B12 and hu23B12 CDR-L2 sequence is FASQSIS (SEQ ID NO. 5). The r23B12 and hu23B12 CDR-L3 sequence is QQTFSLPYT (SEQ ID NO. 6).

The r23B12 variable heavy chain amino acid sequence is EEKLQQSGDD LVRPGAAVKMSCKASGYIFTDYAMH-WVKQRPGQGLEWIGTFIPLLDTSDYNQN-FKGRATLTADKSSNTAYMELSRLTSED-SAVYYCARMGVTHSYVMDAWGQGASVTVS S (SEQ ID NO. 7).

The r23B12 variable light chain amino acid sequence is DIVLTQSPATLSVTPGES-VSLSCRASQPISISVHWFQQKSNESPRL-LIKFASQSISGIPSRFSGSGSGTDFTLN-INRVESEDFSVYYCQQTFSLPYTFGTGTKLELKR (SEQ ID NO. 8).

The nucleic acid sequence for the hu23B12 variable heavy chain is CAG GTG CAG CTG GTG CAG TCT GGC GCT GAG GTG AAG AAG CCT GGC GCC TCC GTG AAG GTC TCC TGC AAG GCT TCT GGC TAC ATC TTC ACC GAC TAC GCC ATG CAC TGG GTG CGG CAG GCC CCT GGC CAG GGG CTG GAG TGG ATG GGT ACC TTC ATC CCT CTG CTG GAC ACC AGC GAC TAC AAC CAG AAC TTC AAG GGC AGA GTC ACC ATG ACC ACA GAC ACA TCC ACC AGC ACA GCC TAC ATG GAG CTG AGG AGC CTG AGA TCT GAC GAC ACC GCC GTG TAT TAC TGT GCC AGA ATG GGA GTG ACC CAC AGC TAC GTG ATG GAT GCA TGG GGC CAG GGC ACC CTG GTC ACC GTC TCC AGC (SEQ ID NO: 9), which encodes the hu23B12 variable heavy chain amino acid sequence QVQLVQSGAEVKKP-GASVKVSCKASGYIFTDYAMH-WVRQAPGQGLEWMGTFIPLLDTSDYNQN-FKGRVTMTTDTSTSTAYMELRSLRSDDTAVYYCARMGVTHSYVMDAWGQ( (SEQ ID NO. 10).

The nucleic acid sequence for the hu23B12 variable light chain is GAA ATT GTG CTG ACT CAG AGC CCA GGC ACC CTG TCT CTG TCT CCA GGC GAG AGA GCC ACC CTC TCC TGC CGG GCC AGC CAG CCC ATC TCC ATC AGC GTG CAC TGG TAC CAG CAG AAA CCA GGA CAG GCT CCA AGG CTG CTG ATC TAC TTT GCC TCC CAG AGC ATC TCC GGG ATC CCC GAT AGG TTC AGC GGA TCC GGA TCT GGG ACA GAT TTC ACC CTC ACC ATC AGC AGA CTG GAG CCT GAA GAT TTC GCA GTG TAT TAC TGT CAG CAG ACC TTC AGC CTG CCT TAC ACT TTC GGC CAA GGG ACC AAG GTG GAG ATC AAG CGT (SEQ ID NO: 11), which encodes the hu23B12 variable light chain amino acid sequence EIVLTQSPGTLSLSPGER-ATLSCRASQPISISVHWYQQK-PGQAPRLLIYFASQSISGIPDRFSGSGS-GTDFTLTISRLEPEDFAVYYCQQTFSLPYTFGQGTKVEIKR (SEQ ID NO. 12).

The nucleic acid sequence for the hu23B12 heavy chain is CAG GTG CAG CTG GTG CAG TCT GGC GCT GAG GTG AAG AAG CCT GGC GCC TCC GTG AAG GTC TCC TGC AAG GCT TCT GGC TAC ATC TTC ACC GAC TAC GCC ATG CAC TGG GTG CGG CAG GCC CCT GGC CAG GGG CTG GAG TGG ATG GGT ACC TTC ATC CCT CTG CTG GAC ACC AGC GAC TAC AAC CAG AAC TTC AAG GGC AGA GTC ACC ATG ACC ACA GAC ACA TCC ACC AGC ACA GCC TAC ATG GAG CTG AGG AGC CTG AGA TCT GAC GAC ACC GCC GTG TAT TAC TGT GCC AGA ATG GGA GTG ACC CAC AGC TAC GTG ATG GAT GCA TGG GGC CAG GGC ACC CTG GTC ACC GTC TCC AGC GCT AGC ACC AAG GGC CCA TCG GTC TTC CCC CTG GCA CCC TCC TCC AAG AGC ACC TCT GGG GGC ACA GCG GCC CTG GGC TGC CTG GTC AAG GAC TAC TTC CCC GAA CCG GTG ACG GTG TCG TGG AAC TCA GGC GCC CTG ACC AGC GGC GTG CAC ACC TTC CCG GCT GTC CTA CAG TCC TCA GGA CTC TAC TCC CTC AGC AGC GTG GTG ACC GTG CCC TCC AGC AGC TTG GGC ACC CAG ACC TAC ATC TGC AAC GTG AAT CAC AAG CCC AGC AAC ACC AAG GTG GAC AAG AAA GTT GAG CCC AAA TCT TGT GAC AAA ACT CAC ACA TGC CCA CCG TGC CCA GCA CCT GAA CTC CTG GGG GGA CCG TCA GTC TTC CTC TTC CCC CCA AAA CCC AAG GAC ACC CTC ATG ATC TCC CGG ACC CCT GAG GTC ACA TGC GTG GTG GTG GAC GTG AGC CAC GAA GAC CCT GAG GTC AAG TTC AAC TGG TAC GTG GAC GGC GTG GAG GTG CAT AAT GCC AAG ACA AAG CCG CGG GAG GAG CAG TAC AAC AGC ACG TAC CGT GTG GTC AGC GTC CTC ACC GTC CTG CAC CAG GAC TGG CTG AAT GGC AAG GAG TAC AAG TGC AAG GTC TCC AAC AAA GCC CTC CCA GCC CCC ATC GAG AAA ACC ATC TCC AAA GCC AAA GGG CAG CCC CGA GAA CCA CAG GTG TAC ACC CTG CCC CCA TCC CGG GAT GAG CTG ACC AAG AAC CAG GTC AGC CTG ACC TGC CTG GTC AAA GGC TTC TAT CCC AGC GAC ATC GCC GTG GAG TGG GAG AGC AAT GGG CAG CCG GAG AAC AAC TAC AAG ACC ACG CCT CCC GTG CTG GAC TCC GAC GGC TCC TTC TTC CTC TAC AGC AAG CTC ACC GTG GAC AAG AGC AGG TGG CAG CAG GGG AAC GTC TTC TCA TGC TCC GTG ATG CAT GAG GCT CTG CAC AAC CAC TAC ACG CAG AAG AGC CTC TCC CTG TCT CCG GGT AAA (SEQ ID NO: 13), which encodes the hu23B12 heavy chain amino acid sequence QVQLVQS-GAEVKKPGASVKVSCKASGYIFTDYAMHWVRQAP-GQGLEWMGTFIPLLDTSDYNQNFKGRVTMTTDTS-TSTAYMELRSLRSDDTAVYYCARMGVTHSYVMDA-WGQGTLVTVSSASTKGPSVFPLAPSSKSTSGGT-AALGCLVKDYFPEPVTVSWNSGALTSGVHTFP-AVLQSSGLYSLSSVVTVPSSSLGTQTYICN-VNHKPSNTKVDKKVEPKSCDKTHTCPPCPAPELL-GGPSVFLFPPKPKDTLMISRTPEVTCVVVDVS-HEDPEVKFNWYVDGVEVHNAKTKPREEQYNS-TYRVVSVLTVLHQDWLNGKEYKCKVSNKALPA-PIEKTISKAKGQPREPQVYTLPPSRD-ELTKNQVSLTCLVKGFYPSDIA-VEWESNGQPENNYKTTPPVLDSDGSFF-LYSKLTVDKSRWQQGNVFSCSVMHEALH-NHYTQKSLSLSPGK (SEQ ID NO: 14).

The nucleic acid sequence for the hu23B12 light chain is GAA ATT GTG CTG ACT CAG AGC CCA GGC ACC CTG TCT CTG TCT CCA GGC GAG AGA GCC ACC CTC TCC TGC CGG GCC AGC CAG CCC ATC TCC ATC AGC GTG CAC TGG TAC CAG CAG AAA CCA GGA CAG GCT CCA AGG CTG CTG ATC TAC TTT GCC TCC CAG AGC ATC TCC GGG ATC CCC GAT AGG TTC AGC GGA TCC GGA TCT GGG ACA GAT TTC ACC CTC ACC ATC AGC AGA CTG GAG CCT GAA GAT TTC GCA GTG TAT TAC TGT CAG CAG ACC TTC AGC CTG CCT TAC ACT TTC GGC CAA GGG ACC AAG GTG GAG ATC AAG CGT ACG GTG GCT GCA CCA TCT GTC TTC ATC TTC CCG CCA TCT GAT GAG CAG TTG AAA TCT GGA ACT GCC TCT GTT GTG TGC CTG CTG AAT AAC TTC TAT CCC AGA GAG GCC AAA GTA CAG TGG AAG GTG GAT AAC GCC CTC CAA TCG GGT AAC TCC CAG GAG AGT GTC ACA GAG CAG GAC AGC AAG GAC AGC ACC TAC AGC CTC AGC AGC ACC CTG ACG CTG AGC AAA GCA GAC TAC GAG AAA CAC AAA GTC TAC GCC TGC GAA GTC ACC CAT CAG GGC CTG AGC TCG CCC GTC ACA AAG AGC TTC AAC AGG GGA GAG TGT (SEQ ID NO: 15), which encodes the hu23B12 light chain amino acid sequence EIVLTQSPGTLSLSPGERATLSCRASQ-PISISVHWYQQKPGQAPRLLIYFASQSISGIPDR-FSGSGSGTDFTLTISRLEPEDFAVYYCQQTFSLP-YTFGQGTKVEIKRTVAAPSVFIFPPSDEQLKS-GTASVVCLLNNFYPREAKVQWKVD-NALQSGNSQESVTEQDSKD-STYSLSSTLTLSKADYEKHKVY-ACEVTHQGLSSPVTKSFNRGEC (SEQ ID NO: 16).

Also contemplated are chimeric antibodies. As noted above, typical chimeric antibodies comprise a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA* 81: 6851-6855).

Bispecific antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan, et al. (1985) *Science* 229: 81. Bispecific antibodies include bispecific antibody fragments. See, e.g., Hollinger, et al. (1993) *Proc. Natl. Acad. Sci. U.S.A.* 90: 6444-48, Gruber, et al., *J. Immunol.* 152: 5368 (1994).

In yet other embodiments, different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

V. Biological Activity of Humanized Anti-TSLP

Antibodies having the characteristics identified herein as being desirable in a humanized anti-TSLP antibody can be screened for inhibitory biologic activity in vitro or for suitable binding affinity. To screen for antibodies that bind to the epitope on human TSLP bound by an antibody of interest (e.g., those which block binding of the cytokine to its receptor), a routine cross-blocking assay such as that described in ANTIBODIES, A LABORATORY MANUAL, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bound at nearby, or even overlapping, epitopes.

Alternatively, epitope mapping, e.g., as described in Champe et al. (1995) *J. Biol. Chem.* 270:1388-1394, can be performed to determine whether the antibody binds an epitope of interest. "Alanine scanning mutagenesis," as described by Cunningham and Wells (1989) *Science* 244: 1081-1085, or some other form of point mutagenesis of amino acid residues in human TSLP may also be used to determine the functional epitope for an anti-TSLP antibody of the present invention. Mutagenesis studies, however, may also reveal amino acid residues that are crucial to the overall three-dimensional structure of TSLP but that are not directly involved in antibody-antigen contacts, and thus other methods may be necessary to confirm a functional epitope determined using this method.

The epitope bound by a specific antibody may also be determined by assessing binding of the antibody to peptides comprising fragments of human TSLP. The amino acid sequence of human TSLP is set forth in SEQ ID NO: 4 in WO 00/17362. A series of overlapping peptides encompassing the sequence of TSLP may be synthesized and screened for binding, e.g. in a direct ELISA, a competitive ELISA (where the peptide is assessed for its ability to prevent binding of an antibody to TSLP bound to a well of a microtiter plate), or on a chip. Such peptide screening methods may not be capable of detecting some discontinuous functional epitopes, i.e. functional epitopes that involve amino acid residues that are not contiguous along the primary sequence of the TSLP polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in TSLP when free and when bound in a complex with an antibody of interest (Zinn-Justin et al. (1992) *Biochemistry* 31, 11335-11347; Zinn-Justin et al. (1993) *Biochemistry* 32, 6884-6891).

With regard to X-ray crystallography, crystallization may be accomplished using any of the known methods in the art (e.g. Giege et al. (1994) *Acta Crystallogr.* D50:339-350; McPherson (1990) *Eur. J. Biochem.* 189:1-23), including microbatch (e.g. Chayen (1997) *Structure* 5:1269-1274), hanging-drop vapor diffusion (e.g. McPherson (1976) *J. Biol. Chem.* 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al., eds., Academic Press; U.S. Patent Application Publication No. 2004/0014194), and BUSTER (Bricogne (1993) *Acta Cryst.* D49:37-60; Bricogne (1997) *Meth. Enzymol.* 276A:361-423, Carter & Sweet, eds.; Roversi et al. (2000) *Acta Cryst.* D56:1313-1323), the disclosures of which are hereby incorporated by reference in their entireties.

Additional antibodies binding to the same epitope as an antibody of the present invention may be obtained, for example, by screening of antibodies raised against TSLP for binding to the epitope, or by immunization of an animal with a peptide comprising a fragment of human TSLP comprising the epitope sequence. Antibodies that bind to the same functional epitope might be expected to exhibit similar biological activities, such as blocking receptor binding, and such activities can be confirmed by functional assays of the antibodies.

Antibody affinities (e.g. for human TSLP) may be determined using standard analysis. Preferred humanized antibodies are those which bind human TSLP with a $K_D$ value of no more than about $1\times10^{-7}$; preferably no more than about $1\times10^{-8}$; more preferably no more than about $1\times10^{-9}$; and most preferably no more than about $1\times10^{-10}$ M.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. Typically, these effects result from the failure of TSLP to bind its receptor. In one embodiment, the antibody and fragments thereof useful in the present compositions and methods inhibit: hTSLP induced proliferation of a Baf-3 cell line transfected with hTSLP-receptor and IL-7Ralpha; hTSLP induced luciferase expression from a Baf-3 cell line transfected with the TSLP-receptor and a luciferase reporter system; hTSLP induced TARC secretion from human primary monocytes isolated from PBMCs; and induction of Th2 differentiation.

As used herein, the term "specific" refers to the selective binding of the antibody to the target antigen epitope. Antibodies can be tested for specificity of binding by comparing binding to TSLP to binding to irrelevant antigen or antigen mixture under a given set of conditions. If the antibody binds to TSLP at least 10, and preferably 50 times more than to irrelevant antigen or antigen mixture then it is considered to be specific. An antibody that "specifically binds" to TSLP does not bind to proteins that do not comprise the TSLP-derived sequences, i.e. "specificity" as used herein relates to TSLP specificity, and not any other sequences that may be present in the protein in question. For example, as used herein, an antibody that "specifically binds" to TSLP will typically bind to FLAG-h TSLP, which is a fusion protein comprising TSLP and a FLAG® peptide tag, but it does not bind to the FLAG® peptide tag alone or when it is fused to a protein other than TSLP.

VI. Pharmaceutical Compositions

To prepare pharmaceutical or sterile compositions, the antibody or fragment thereof is admixed with a pharmaceutically acceptable carrier or excipient, see, e.g., *Remington's Pharmaceutical Sciences and U.S. Pharmacopeia: National Formulary*, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Antibodies exhibiting high therapeutic indices are preferred. The data obtained from these cell culture assays and animal studies can be used in formulating a range of dosage for use in humans.

The dosage of such compounds lies preferably within a range of circulating concentrations that include the $ED_{50}$ with little or no toxicity. The dosage may vary within this range depending upon the dosage form employed and the route of administration utilized.

Suitable routes of administration include parenteral administration, such as intramuscular, intravenous, or subcutaneous administration. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection. In one embodiment, the binding compound of the invention is administered intravenously. In another embodiment, the binding compound of the invention is administered subcutaneously.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348: 601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing an inflammatory, autoimmune, or proliferative response to the reagent.

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 μg/kg body weight, more generally at least 0.2 μg/kg, most generally at least 0.5 μg/kg, typically at least 1 μg/kg, more typically at least 10 μg/kg, most typically at least 100 μg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an inflammatory disease.

As used herein, the term "therapeutically effective amount" or "effective amount" refers to an amount of an anti-TSLP antibody or fragment thereof, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent, e.g., a cytokine, steroid, chemotherapeutic agent, antibiotic, or radiation, are well known in the art, see, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., PA. The pharmaceutical composition of the invention may also contain other immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., inflixmab, etanercept), mycophenolate mofetil, 15-deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

Typical veterinary, experimental, or research subjects include monkeys, dogs, cats, rats, mice, rabbits, guinea pigs, horses, and humans VII. Antibody Production For recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of the humanized anti-TSLP antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, Spodoptera frugiperda ovarian (SD) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast Pichia pastoris, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of the anti-TSLP antibody are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for TSLP) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VIII. Uses

The present invention provides methods for using engineered anti-TSLP for the treatment and diagnosis of inflammatory disorders.

In a preferred embodiment, the inflammatory disorder is asthma.

In another preferred embodiment, the inflammatory disorder is an allergic inflammatory disorder. In a preferred embodiment, the allergic inflammatory disorder is allergic rhinosinusitis, allergic asthma, allergic conjunctivitis, or atopic dermatitis.

The present invention provides methods for using engineered anti-TSLP for the treatment and diagnosis of fibrosis, inflammatory bowel disease, Hodgkin's lymphoma, respiratory viral infections or other viral infections, rheumatoid arthritis, or any other disorder characterized by inflammation at the site of injury.

The broad scope of this invention is best understood with reference to the following examples, which are not intended to limit the inventions to the specific embodiments.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

EXAMPLE 1

General Methods

Standard methods in molecular biology are described (Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan et al. (2000) *Current Protocols in Protein Science, Vol.* 2, John Wiley and Sons, Inc., New York; Ausubel et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan et al. (2001) *Current Protcols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan et al. (2001) *Current Protcols in Immunology, Vol.* 4, John Wiley, Inc., New York).

Methods for flow cytometry, including fluorescence activated cell sorting (FACS), are available (see, e.g., Owens et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, PA; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLE 2

Humanization of Anti-Human TSLP Antibodies

Rat anti-human TSLP antibody 23B12 is produced by the hybridoma deposited at the American Type Culture Collection (10801 University Blvd., Manassas, Va. 20110-2209 USA) ("ATCC") with the patent deposit designation "PTA-7951." The hybridoma was deposited on Oct. 26, 2006 under the conditions of the Budapest Treaty, and received accession number PTA-7951. The humanization of rat anti-human TSLP antibody 23B12 was performed as essentially as described in PCT patent application publications WO 2005/047324 and WO 2005/047326, which are incorporated by reference.

Variable light and heavy domains of the anti-TSLP monoclonal antibody (23B12) were cloned and fused to a human kappa light chain (CL domain) and human IgG1 heavy chain (CH1-hinge-CH2-CH3), respectively.

The amino acid sequence of the non-human VH domain was compared to a group of three human VH germline amino acid sequences; one representative from each of subgroups IGHV1, IGHV3 and IGHV4. The VH subgroups are listed in M.-P. Lefranc, "Nomenclature of the Human Immunoglobulin Heavy (IGH) Genes", *Experimental and Clinical Immunogenetics*, 18:100-116, 2001. Rat 23B12 antibody scored highest against human heavy chain germline DP-14 in subgroup VH1.

For the rat 23B12 antibody, the VL sequence was of the kappa subclass of VL. The amino acid sequence of the non-human VL domain was compared to a group of four human VL kappa germline amino acid sequences. The group of four is comprised of one representative from each of four established human VL subgroups listed in V. Barbie & M.-P. Lefranc, "The Human Immunoglobulin Kappa Variable (IGKV) Genes and Joining (IGKJ) Segments", *Experimental and Clinical Immunogenetics*, 15:171-183, 1998 and M.-P. Lefranc, "Nomenclature of the Human Immunoglobulin Kappa (IGK) Genes", *Experimental and Clinical Immunogenetics*, 18:161-174, 2001. The four subgroups also correspond to the four subgroups listed in Kabat et al. "Sequences of Proteins of Immunological Interest", U.S. Department of Health and Human Services, NIH Pub. 91-3242, 5th Ed., 1991, pp. 103-130. Rat 23B12 antibody scored highest against human light chain germline Z-A27 in subgroup VLkIII.

Once the target amino acid sequences of the variable heavy and light chains were determined, plasmids encoding the full-length humanized antibody were generated. Starting with a plasmid encoding a humanized anti-IL-23 antibody having VH1 DP-14 germline framework and a separate plasmid encoding a humanized anti-IGFR antibody having VLkIII Z-A27 germline framework, the plasmids were altered using Kunkel mutagenesis (see, e.g., Kunkel T A. (1985) *Proc. Natl. Acad. Sci. U.S.A* 82:488-492) to change the DNA sequence to the target humanized 23B12 sequence. Simultaneously, codon optimization was incorporated into the changes to provide for potentially optimal expression. The humanized heavy and light variable chain amino acid sequences, are set forth in SEQ ID NOs: 10 and 12. The full-length humanized heavy and light chain amino acid sequences, are set forth in SEQ ID NOs: 14 and 16. A variant of the light chain was also created, wherein the variant comprised a K (rather than a Y) at amino acid position 49 of SEQ ID NO:12 or SEQ ID NO:16.

EXAMPLE 3

Determining the Equilibrium Dissociation Constant ($K_D$) for Humanized Anti-Human TSLP Using KinExA Technology The equilibrium dissociation constant ($K_D$) was determined using the KinExA 3000 instrument (Sapidyne Instruments Inc., www.sapidyne.com). The KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag]=k_{off}[AbAg]$$

2. Antibody and antigen bind 1:1 and total antibody equals antigen-antibody complex plus free antibody.
3. Instrument signal is linearly related to free antibody concentration.

Materials
Antibodies:
Rat anti hu TSLP mAb 23B12.H8.A4 (SPB Lot PAB330)
Rat anti hu TSLP mAb 23B12.H8.A4 (SPB Lot PAB330A)
Humanized anti hu TSLP mAb 23B12 (VL Y49)
Humanized anti hu TSLP mAb 23B12 (VL K49)
Humanized anti hu TSLP mAb 23B12 (VL Y49)
Antigens:
Recombinant human TSLP (SPB Lot P345)
Recombinant human TSLP (SPB Lot P367)
Recombinant human TSLP (R&D, Cat.N. 1398-TS/CF, Lot IDK 015031)
Biotinylated Antigens:
Biotinylated human TSLP (SPB Lot p367AC)
Biotinylated human TSLP (SPB Lot p367AA)
Biotinylated human TSLP (SPB Lot 38ABMA)
Other Reagents:
PMMA particles, 98 micron (Sapidyne, Cat No. 440198)
Neutravidin (Pierce, Cat No. 31000)
Cy5-conjugated Goat anti-rat IgG (H+L) (Jackson Immunoresearch Laboratories Cat. No 112-175-167, Lot 60306)
Cy5-conjugated Goat anti-HuIgG (H+L) (Jackson Immunoresearch Laboratories Cat. No 109-175-088, lot 49069 and lot 58552)

EXPERIMENTAL CONDITIONS

PMMA particles were coated with biotinylated human TSLP according to Sapidyne "Protocol for coating PMMA particles with biotinylated ligands having short or nonexistent linker arms". All experimental procedures were done according to the KinExA 3000 manual. All runs were done in duplicate.

For Rat anti hu TSLP mAb 23B12.H8.A4 (SPB Lot PAB330) the following conditions were used:
Sample volume: 2 mL
Sample flow rate: 0.25 mL/min
Label volume: 1 mL
Label flow rate: 0.25 mL/min
Antibody conc.: 0.1 nM
Highest antigen conc.: 10 nM
Lowest antigen conc.: 10 pM
For Rat anti hu TSLP mAb 23B12.H8.A4 (SPB Lot PAB330A) the following conditions were used:
Sample volume: 4 mL
Sample flow rate: 0.25 mL/min
Label volume: 1 mL
Label flow rate: 0.25 mL/min
Antibody conc.: 0.05 nM
Highest antigen conc.: 0.5 nM
Lowest antigen conc.: 0.5 pM
For Humanized anti hu TSLP mAbs the following conditions were used:
Sample volume: 2 mL
Sample flow rate: 0.25 mL/min
Label volume: 1 mL
Label flow rate: 0.25 mL/min
Antibody conc.: 0.02 nM
Highest antigen conc.: 0.2 nM
Lowest antigen conc.: 0.2 pM
Two-fold serial dilutions of the antigen were prepared and mixed with the antibody at constant concentration. The mixture was incubated for 2 hours at 25° C. to equilibrate.

Table 4 shows the results of the KinExA analysis.

TABLE 4

$K_D$ Values Determined by KinExa

| mAb | TSLP | Expression | $K_D$ (pM) |
|---|---|---|---|
| rat 23B12.H8.H4 | human | HEK293 | 0.22 |
| rat 23B12.H8.H4 | human | E. coli | 0.47 |
| hu23B12(VL Y49) | human | HEK293 | 2.1 |
| hu23B12(VL K49) | human | HEK293 | 1.0 |
| hu23B12(VL Y49) | human | E. coli | 1.7 |

EXAMPLE 4

Determining the $EC_{50}$ for Humanized Anti-Human TSLP Using ELISA

The ELISA measures the EC50 of rat 23B12 purified from hybridoma supernatant or recombinant humanized 23B12 IgG1 binding to either adenovirus-derived human TSLP (S-P Biopharma) or E. coli-derived human TSLP (S-P Biopharma or R&D 1398-TS).

Materials:
Nunc Maxisorb 96 well Immunoplate cert. (Nunc #439454)
0× phosphate-buffered saline (PBS), pH 7.4 (Fisher #BP399-20)
20× Tris Buffered Saline (TBS), pH 7.4 (Technova #1680)
Tween-20, enzyme grade (Fisher #BP337-500)
500 mM EDTA (Technova #E0306)
Albumin, bovine serum RIA grade (Sigma #A7888)
Coating Buffer: 1 µg/mL TSLP in PBS at 100 µL/well
Detection Reagent:
HRP-F(ab)'2 goat anti-human IgG H+L (Jackson #109-036-088);
HRP-F(ab)'2 goat anti-rat IgG H+L (Jackson #112-032-072)
Substrate & Stop Solutions:
TMB Microwell Peroxidase Substrate System 2C (Kirkegaard & Perry Labs #50-76-00) 1:1; 1M $H_3PO_4$ 0.1 mL/well
ABTS (Kirkegaard & Perry Labs #50-66-06) 100 µL/well
ABTS Peroxidase stop solution (Kirkegaard & Perry Labs #50-085-02) 5× concentrate diluter 1:5 in MIlli-Q water, 100 µL/well
ELISA Diluent and Assay Buffer:
50 mM TBS or PBS;0.5% BSA;0.05% Tween-20; 4 mM EDTA
ELISA Wash Buffer:
50 mM TBS or PBS;0.05% Tween-20; 4 mM EDTA
Equipment:
Skatron Scanwasher300™
Molecular Devices VersaMax™ microplate reader
Protocol
Coating of plates was performed as follows: TSLP (100 or 200 ng per well) in PBS was incubated at 4° C. overnight. Plates were washed with 1 cycle (4 washes/cycle) on a Skatron plate washer, blocked by addition of 0.2 mL/well ELISA assay buffer, incubated for 60 min at 25° C. on an orbital shaker and then washed for 1 cycle. Antibody was then titrated across a row of eight wells in the range of 1000 ng/mL to 0.4572 ng/mL using serial 3-fold dilutions and incubated for 90 min. at 25° C. on an orbital shaker. Plates were washed for 1 cycle, HRP-goat F(ab')$_2$ anti-human or anti-rat IgG (H+L) (1:5,000 dilution) was added at 0.1 mL/well and incubated for 60 min at 25° C. on an orbital shaker. Plates were washed for 2 cycles with plate rotation between cycles. TMB or ABTS substrate was added at 0.1 mL/well and incubated 5 min on orbital shaker. Stop solution was then added at 0.1 mL/well and the plates read at $A_{450\text{-}570\ nm}$ (TMB) or $A_{405\ nm}$ (ABTS).

Table 5 shows the results of the ELISA analysis.

TABLE 5

$EC_{50}$ Values Determined By ELISA

| mAb | TSLP Species | TSLP Expression[1] | $EC_{50}$ (nM) |
|---|---|---|---|
| rat 23B12.H8.H4 | human | HEK293-B | 0.79 |
| rat 23B12.H8.H4 | human | HEK293 | 0.37 |
| rat 23B12.H8.H4 | human | HEK293-F | 0.26 |
| | | | 0.47 ± 0.28 (n = 3) |
| rat 23B12.H8.H4 | human | E. coli-B | 0.40 |
| rat 23B12.H8.H4 | human | E. coli-B | 0.39 |
| | | | 0.44 ± 0.20 (n = 5) |
| hu23B12(VL Y49) | human | HEK293-B | 0.22 |
| hu23B12(VL Y49) | human | HEK293 | 0.029 |
| hu23B12(VL Y49) | human | HEK293-F | 0.018 |
| hu23B12(VL Y49) | human | HEK293 | 0.17 |
| hu23B12(VL Y49) | human | HEK293 | 0.21 |
| hu23B12(VL Y49) | human | HEK293 | 0.11 |
| hu23B12(VL Y49) | human | HEK293 | 0.13 |
| hu23B12(VL Y49) | human | HEK293 | 0.15 |
| hu23B12(VL Y49) | human | HEK293 | 0.24 |
| hu23B12(VL Y49) | human | HEK293 | 0.18 |
| hu23B12(VL Y49) | human | HEK293 | 0.11 |
| hu23B12(VL Y49) | human | HEK293[2] | 0.073 |
| | | | 0.14 ± 0.07 (n = 12) |
| hu23B12(VL Y49) | human | E. coli-B | 0.064 |
| hu23B12(VL Y49) | human | E. coli-B | 0.085 |
| hu23B12(VL Y49) | human | E. coli | 0.11 |
| hu23B12(VL Y49) | human | E. coli | 0.11 |
| hu23B12(VL Y49) | human | E. coli | 0.060 |
| hu23B12(VL Y49) | human | E. coli[2] | 0.061 |
| hu23B12(VL Y49) | human | E. coli[2] | 0.029 |
| | | | 0.07 ± 0.03 (n = 7) |
| | | | 0.11 ± 0.07 (n = 19) |
| hu23B12(VL Y49) | cyno | HEK293 | 0.45 |
| hu23B12(VL Y49) | cyno | HEK293 | 0.52 |
| hu23B12(VL Y49) | cyno | HEK293 | 0.29 |
| hu23B12(VL Y49) | cyno | HEK293 | 0.15 |
| hu23B12(VL Y49) | cyno | HEK293 | 0.19 |
| hu23B12(VL Y49) | cyno | HEK293 | 0.27 |
| | | | 0.31 ± 0.15 (n = 6) |
| hu23B12(VL K49) | human | HEK293-B | 0.12 |
| hu23B12(VL K49) | human | E. coli-B | 0.038 |
| hu23B12(VL K49) | human | E. coli-B | 0.050 |
| hu23B12(VL K49) | human | HEK293 | 0.034 |
| hu23B12(VL K49) | human | HEK293-F | 0.021 |
| | | | 0.05 ± 0.04 (n = 5) |

[1]-B = TSLP biotinylated -F = TSLP removal of furin cleavage site via K101A/R102A
[2]direct coat of 200 ng TSLP instead of 100 ng

EXAMPLE 5

Affinity of Rat 23B12 And Humanized 23B12 Antibodies for Human and Cyno TSLP

The kinetic binding activities of the parental rat and its humanized derivative anti human TSLP antibody 23B12 against both human (hu) and cynomolgus monkey (cyno) TSLP were measured by surface plasmon resonance using a BIAcore T100 system (BIAcore AB, Upsalla, Sweden). Approximately 100RUs of human TSLP or cyno TSLP were immobilized via amine coupling chemistry onto a Sensor Chip CM5 (Research grade, BR-1006-68). HBS-EP buffer (BR-1006-69) was used as the running buffer with a flow rate of 30 µL/min. rat and humanized 23B12 antibodies at varying concentrations ranging from 0.82 to 600 nM were injected over the immobilized hu or cyno TSLP surfaces at a flow rate of 30 µL/min. Following each injection cycle the CM5 chip surface was regenerated using a series of solutions (10 mM Glycine pH 1.5 and 25 mM NaOH respectively) at a flow rate of 75 µL/min Background subtraction binding sensorgrams were used for analyzing the rate constant of association (ka) and dissociation (kd), and the equilibrium dissociation constant $K_D$. The resulting data sets were fitted with a bivalent analyte model using the BIAevaluation software (version 1.0). The $K_D$ determined for the parental rat 23B12 antibody against human TSLP was 64 pM, while the respective value against the cyno TSLP ligand was 86 pM (Table 6). The $K_D$ determined for the humanized 23B12 antibody against human TSLP was 111 pM, while the respective value against the cyno TSLP ligand was 132 pM (Table 6), indicating a less than two fold loss of affinity upon humanization of 23B12 mAb.

TABLE 6

BIAcore Analysis

| Antibody | Ligand | ka (1/Ms) | kd (1/s) | $K_D$ (pM) |
|---|---|---|---|---|
| rat 23B12 | huTSLP | 3.18E+05 | 2.1E−05 | 64 |
| | cynoTSLP | 1.86E+05 | 1.6E−05 | 86 |
| hu 23B12 | huTSLP | 5.00E+05 | 5.6E−05 | 111 |
| | cynoTSLP | 3.57E+05 | 4.7E−05 | 132 |

EXAMPLE 6

Proliferation Bioassay for the Assessment of Neutralizing Anti-TSLP Antibody

The ability of a monoclonal antibody to biologically neutralize TSLP was assessed by the application of short-term proliferation bioassays that utilize cells which express recombinant TSLP receptors. The transfectant Ba/F3-TSLPR-IL7Ra cells proliferate in response to TSLP and the response can be inhibited by a neutralizing anti-TSLP antibody. Each antibody was titrated against a concentration of TSLP chosen within the linear region of the TSLP dose-response curve, near plateau and above the TSLP $EC_{50}$. Proliferation, or lack thereof, is measured by colorimetric means using Alamar Blue, a growth indicator dye based on detection of metabolic activity. The ability of an antibody to neutralize TSLP is assessed by its EC50 value, or concentration of antibody that induces half-maximal inhibition of TSLP proliferation.

Ba/F3 transfectants are maintained in RPMI-1640 medium, 10% fetal calf serum, 50 µM 2-mercaptoethanol, 2 mM L-Glutamine, 50 µg/mL penicillin-streptomycin, and 10 ng/mL mouse IL-3.

Ba/F3 proliferation bioassays are performed in RPMI-1640 medium, 10% fetal calf serum, 50 µM 2-mercaptoethanol, 2 mM L-Glutamine, and 50 µg/mL penicillin-streptomycin.

The assay is performed in 96-well flat bottom plates (Falcon 3072 or similar). All preparations of reagents and cell suspensions utilize the appropriate bioassay medium. The assay volume is 150 μL per well. Titrations of an anti-TSLP antibody are pre-incubated with TSLP for 30-60 minutes at room temperature, during which time cells are prepared. Cells are added to plates following the antibody-cytokine pre-incubation. Bioassay plates are incubated in a humidified tissue culture chamber (37 C, 5% $CO_2$) for 40-48 hours. At the end of the culture time, Alamar Blue (Biosource Cat #DAL1100) is added and allowed to develop for 8-12 hours. Absorbance is then read at 570 nm and 600 nm (VERSAmax Microplate Reader, Molecular Probes), and an $OD_{570-600}$ is obtained. Duplicates or triplicates are recommended.

Cells are used in a healthy growth state, generally at densities of $3-8\times10^5$/mL. Cells are counted, pelleted, washed twice in bioassay medium, and suspended to the appropriate density for plating.

TSLP was prepared to working concentration and added to first well at 75 pt. Serial dilutions of 1:3 were made by titrating 25:50 μL in bioassay medium across wells, leaving 50 μL/well. Cells were suspended to the appropriate density for plating at 100 μL per well.

The antibody was prepared to working concentration and added to the first well at 75 μL. Serial dilutions of 1:3 were made by titrating 25:50 μL in bioassay medium across wells, leaving 50 μL per well. TSLP at the appropriate concentration was added at 50 μL per well to the wells containing the titrated antibody. Cells were suspended to the appropriate density for plating at 50 μL per well, and added following the antibody-cytokine pre-incubation.

Using GraphPad Prism 3.0 software, absorbance was plotted against cytokine or antibody concentration and EC50 values were determined using non-linear regression (curve fit) of sigmoidal dose-response.

The assay results are shown in Table 7.

TABLE 7

Inhibition Of Proliferation

| mAb | TSLP Species | TSLP Expression | EC50 (nM) |
|---|---|---|---|
| rat 23B12.H8.H4 | human | HEK293 | 0.093 |
| rat 23B12.H8.H4 | human | HEK293 | 0.085 |
| rat 23B12.H8.H4 | human | HEK293 | 0.23 |
| rat 23B12.H8.H4 | human | HEK293 | 0.040 |
| rat 23B12.H8.H4 | human | HEK293 | 0.10 |
|  |  |  | 0.11 ± 0.07 (n = 5) |
| rat 23B12.H8.H4 | human | E. coli | 2.16 |
| rat 23B12.H8.H4 | human | E. coli | 2.78 |
| rat 23B12.H8.H4 | human | E. coli | 4.15 |
| rat 23B12.H8.H4 | human | E. coli | 3.81 |
| rat 23B12.H8.H4 | human | E. coli | 1.83 |
| rat 23B12.H8.H4 | human | E. coli | 3.46 |
| rat 23B12.H8.H4 | human | E. coli | 2.77 |
| rat 23B12.H8.H4 | human | E. coli | 3.10 |
|  |  |  | 3.01 ± 0.79 (n = 8) |
| rat 23B12.H8.H4 | cyno | HEK293 | 0.45 |
| rat 23B12.H8.H4 | cyno | HEK293 | 0.42 |
| rat 23B12.H8.H4 | cyno | HEK293 | 0.61 |
| rat 23B12.H8.H4 | cyno | HEK293 | 0.77 |
|  |  |  | 0.56 ± 0.16 (n = 4) |

EXAMPLE 7

Neutralizing Activity of Anti-TSLP mAb r23B12 on TSLP Induced TARC Production by Human Primary Dendritic Cells Peripheral blood mononuclear cells (PBMCs) were isolated from buffy coats obtained from healthy blood donors (Stanford Medical School Blood Center, Stanford, Calif.) by Ficoll centrifugation and CD11c+ Dendritic Cells were obtained by MACS (Miltenyi Biotech, Auburn, Calif.) using negative selection followed by cell sorting using a FACS. Lineage negative (Lin⁻) cells were obtained by MACS depletion of T cells, B cells, NK cells, red blood cells and monocytes form PBMC using mouse anti-human CD3 mAb (OKT3, DNAX) and mouse anti-CD16 mAb and goat anti-mouse IgG coated magnetic beads (Miltenyi Biotech), and using magnetic beads directly coated with anti-CD19, CD56 and CD14 mAbs (Miltenyi Biotech). Subsequently, Lin⁻ cells were stained with TC-anti-CD4 (Caltag, Burlingame, Calif.), PE-anti-CD11c and FITC-anti-CD3, —CD14, —CD19, —CD56, —CD16, and —CD20 (all BD Biosciences, San Diego, Calif.) and CD11c+ DC sorted on a Vantage FACsorter™ (BD Biosciences) to a purity >99% of $CD11c^+ CD4^+ Lin^-$ cells.

$CD11c^+ CD4^+$ DCs were cultured immediately after sorting in RPMI (Mediatech, Herndon, Va.) containing 10% FCS and 1% pyruvate (Mediatech), HEPES (Invitrogen, Grand Island, N.Y.) and penicillin-streptomycin (Mediatech). Cells were seeded at $0.5\times10^6$/ml in flat-bottomed 96-well plates in the presence of medium alone, TSLP (15 ng/ml, DNAX), or in a combination of TSLP and the neutralizing anti-TSLP mAb (clone 23B12) or an anti-TSLPR monoclonal antibody or an isotype control rat IgG2a (R&D Systems, Minneapolis, Minn.). DC culture supernatants were collected after 24 h of culture, stored frozen at −20° C. and analyzed for TARC protein levels by ELISA (R&D Systems).

The results are provided in Table 8.

TABLE 8

|  | TARC (pg/ml) |
|---|---|
| DC | 5 |
| TSLP-DC | 1400.5 |
| TSLP + 5 μg/ml r23B12 antibody | 41.5 |
| TSLP + 0.5 μg/ml r23B12 antibody | 146 |
| TSLP + 0.05 μg/ml r23B12 antibody | 570.5 |
| TSLP + 20 μg/ml r23B12 antibody | 199 |

CD11c+ DC cultured in media alone do not produce significant levels of TARC. The addition of TSLP (15 ng/ml) to CD11c+ DC induced significant levels of TARC production up to ~1500 pg/ml. This TSLP mediated induction of TARC was blocked in a dose dependent manner by the simultaneous addition of anti-TSLP mAb 23B12.

EXAMPLE 8

Neutralizing Activity of Anti-TSLP mAb r23B12 on TSLP Induced Th2 Differentiation by Human Primary Dendritic Cells Peripheral blood mononuclear cells (PBMCs) were isolated from buffy coats obtained from healthy blood donors (Stanford Medical School Blood Center, Stanford, Calif.) by Ficoll centrifugation and CD11c+ Dendritic Cells were obtained by MACS (Miltenyi Biotech, Auburn, Calif.) using negative selection followed by cell sorting using a FACS. Lineage negative (Lin⁻) cells were obtained by MACS depletion of T cells, B cells, NK cells, red blood cells and monocytes form PBMC using mouse anti-human CD3 mAb (OKT3, DNAX) and mouse anti-CD16 mAb and goat anti-mouse IgG coated magnetic beads (Miltenyi Biotech), and using magnetic beads directly coated with anti-CD19, CD56 and CD14 mAbs (Miltenyi Biotech). Subsequently, Lin⁻ cells were stained with TC-anti-CD4 (Caltag, Burlingame, Calif.), PE-anti-CD11c and FITC-anti-CD3, —CD14, —CD19, —CD56, —CD16, and —CD20 (all BD Biosciences, San Diego, Calif.) and CD11c+ DC sorted on a Vantage FACsorter™ (BD Biosciences) to a purity >99% of CD11c+ CD4+ Lin− cells.

CD11c+ CD4+ DCs were cultured immediately after sorting in RPMI (Mediatech, Herndon, Va.) containing 10% FCS and 1% pyruvate (Mediatech), HEPES (Invitrogen, Grand Island, N.Y.) and penicillin-streptomycin (Mediatech). Cells were seeded at $0.5 \times 10^6$/ml in flat-bottomed 96-well plates in the presence of medium alone, TSLP (15 ng/ml, DNAX), or in a combination of TSLP and the neutralizing anti-TSLP mAb (clone 23B12) or the anti-TSLPR monoclonal antibody or an isotype control rat IgG2a (R&D Systems, Minneapolis, Minn.). CD11c+ DCs were collected after 24 h of culture under the different conditions, washed twice and recultured with allogeneic CD4+ CD45RA+ naïve T cells.

CD4+ CD45RA+ naïve T cells were isolated by cell sorting after negative depletion of CD8, CD16, CD20, CD19, CD56 and CD14 cells using magnetic beads (Myltenyi Biotech). After 24 h of culture under different conditions, CD11c+ DCs were collected, washed twice, and co-cultured with $5 \times 10^4$ allogeneic naive CD4+ T cells in round-bottomed 96-well plates at a ratio of 1:5 DC:T cells. After 6 d. of culture, supernatants were collected and frozen at −20° C. and numbers of viable cells determined by trypan blue exclusion. To test their capacity to secrete cytokines, DC-primed CD4+ T cells ($10^6$/ml) were restimulated with biotinylated anti-CD3 (10 ng/ml) mAbs crosslinked to streptavidin coated tissue culture plates in the presence of soluble anti-CD28 mAbs (1000 ng/ml). Culture supernatants were collected after 24 hrs of culture, frozen at −20° C. or analyzed by Luminex assay for IFNγ-, TNFα-, IL-2, IL-4, IL-5, IL-10 and IL-13 (Linco Research Inc., St Charles, Mo.).

The results are provided in Table 9.

TABLE 9

| Cytokine Production | DC + CD4 | TSLP-DC + CD4 | TSLP-DC + 5 µg/ml r23B12 + CD4 | TSLP-DC + 0.5 µg/ml r23B12 + CD4 | TSLP-DC + 0.05 µg/ml r23B12 + CD4 |
|---|---|---|---|---|---|
| IL-5 (pg/ml) | 115 | 777 | 24 | 70.6 | 32 |
| IL-4 (pg/ml) | 14 | 89 | 14.5 | 21.3 | 27.3 |
| IL-13 (pg/ml) | 136 | 1290 | 55.5 | 182 | 43.3 |

The coculture of naïve CD4+ CD45RA+ T cells with CD11c+ DC that had been cultured in media alone resulted in a T cell population, that upon reactivation by anti-CD3+ anti-CD28 mAbs, produced low levels of Th2 cytokines. Addition of TSLP (15 ng/ml) to the primary CD11c+ DC culture induced the production of significant levels of IL-4, IL-5 and IL-13 by the responding T cells, suggesting that TSLP-DC induced the differentiation of naïve T cells towards Th2 cells. This TSLP mediated induction of Th2 differentiation was blocked in a dose dependent manner by the simultaneous addition of anti-TSLP mAb 23B12 to the primary DC cultures.

EXAMPLE 9

Cyno-ization of Anti-Human TSLP Antibodies

Two studies have shown that cynomolgus monkeys (*Macaca fascicularis*) VL are similar to human VLκ-I and that cynomolgus VH are similar to human VH-III (41%), VH-IV (39%), and VH-I (14%). (Lewis et al., Dev. Comp. Immunol. 17:549-560 (1993); and Druar et al., Immunogentics 57:730-738 (2005).) In order to minimize potential immunogenicity of hu23B12 in cymomolgus monkeys, the rat 23B12 CDRs were transferred onto human VLκ-I and VH-III frameworks; these were then fused onto cynomolgus IgG constant domains.

The amino acid sequence of the cyno-ized light chain is MAPVQLLGLLVLFLPAMRCDIQMTQSPSSLSASVGD-RVTITCRASQPISISVHWYQQKPGKAPKLLIYFAS-QSISGVPSRFSGSGSGTDFTLTISSLQPEDFATY-YCQQTFSLPYTFGQGTKVEIKRTVAAPS-VFIFPPSEDQVKSGTVSVVCLLNNFYPREA-SVKWKVDGVLKTGNSQESVTEQDSKDN-TYSLSSTLTLSSTDYQSHNVY-ACEVTHQGLSSPVTKSFNRGEC (SEQ ID NO: 17). The signal sequence is underlined.

The amino acid sequence of the cyno-ized heavy chain is MAVLGLLFCLVTFPSCVLSQVQLVESGGGVVQPGRS-LRLSCAASGYIFTDYAMHWVRQAPGK-GLEWVATFIPLLDTSDYNQNFKGRFTIS-RDNSKNTLYLQMNSLRAEDTAVYYC ARMGVTH-SYVMDAWGQGTLVTVSSASTKGPSVFPLAPSSRSTS-ESTAALGCLVKDYFPEP-VTVSWNSGSLTSGVHTFPAVLQSS-GLYSLSSVVTVPSSSLGTQTYVCNVNH-KPSNTKVDKRVEIKTCGGGSKPPTCPPCPAPELLGGP-SVFLFPPKPKDTLMISRTPEVTCVVVD-VSQEDPDVKFNWYVNGAEVHHAQTK-PRETQYNSTYRVVSVLTVTHQDWL-NGKEYTCKVSNKALPAPIQKTISKDKGQPREPQVYT-LPPSREELTKNQVSLTCLVKGFYPSDI-VVEWESSGQPENTYKTTPPVLDSDGSY-FLYSKLTVDKSRWQQGNVFSCSVM-HEALHNHYTQKSLSLSPGK (SEQ ID NO:18). The signal sequence is underlined.

Cyno-ized anti-human TSLP 23B12 antibodies were then recombinantly produced in CHO cells.

EXAMPLE 10

Proliferation Bioassay for the Assessment of the Neutralizing Activity of Cyno-ized Anti-Human TSLP Antibodies The ability of cyno-ized anti-human TSLP 23B12 antibodies to biologically neutralize human or cyno TSLP was assessed by the application of short-term proliferation bioassays that utilize cells which express recombinant TSLP receptors. The transfectant Ba/F3-huTSLPR/huIL-7Ra and Ba/F3-cyTSLPR/cyIL-7Ra cells proliferate in response to human TSLP and cyno TSLP, and the response can be inhibited by a neutralizing anti-TSLP antibody. An antibody is titrated against a concentration of human or cyno TSLP chosen within the linear region of the dose-response curve, near plateau and above EC50. Proliferation, or lack thereof, is measured by colorimetric means using Alamar Blue, a growth indicator dye based on detection of metabolic activity. The ability of an antibody to neutralize TSLP is assessed by its EC50 value, or concentration of antibody that induces half-maximal inhibition of TSLP proliferation.

Ba/F3 transfectants are maintained in RPMI-1640 medium, 10% fetal bovine serum, 50 uM 2-mercaptoethanol, 2 mM L-Glutamine, 50 ug/mL penicillin-streptomycin, 10 ng/mL mouse IL-3, 1 mg/ml G418, and 2 ug/ml puromycin.

Ba/F3 proliferation bioassays are performed in RPMI-1640 medium, 10% fetal bovine serum, 50 uM 2-mercaptoethanol, 2 mM L-Glutamine, and 50 ug/mL penicillin-streptomycin.

The assays were performed in 96-well flat bottom plates (Falcon 3072 or similar). All preparations of reagents and cell suspensions utilized the appropriate bioassay medium. The assay volume was 150 uL per well. Titrations of an anti-TSLP antibody were pre-incubated with huTSLP or cyTSLP for approximately 30 minutes at room temperature, during which time cells were prepared. Cells were added to plates following the antibody-cytokine pre-incubation. Bioassay plates were incubated in a humidified tissue culture chamber (37 C, 5% $CO_2$) for 40-48 hr. At the end of the culture time, Alamar Blue (Biosource Cat #DAL1100) was added at 16.5 uL/well and allowed to develop for 5-12 hours. Absorbance was then read at 570 nm and 600 nm (VERSAmax Microplate Reader, Molecular Devices), and an $OD_{570-600}$ was obtained. Duplicates were run for each sample.

Cells are used in a healthy growth state, generally at densities of $7-9\times10^5$/mL. Cells are washed twice in bioassay medium, counted, and suspended to the appropriate density for plating at 7500 cells/50 ul per well.

Human or cyno TSLP was prepared to working concentration (600 ng/mL) and added to first well at 75 uL. Serial dilutions of 1:3 were made by titrating 25:50 uL in bioassay medium across wells, leaving 50 uL/well. Cells were suspended to the appropriate density for plating at 7500 cells/50 uL per well. To substitute the addition of antibody, 50 ul of bioassay medium was added to these wells to bring the final volume to 150 ul.

The antibody was prepared to working concentration (3× the final concentration; the final starting concentration of each antibody varied) and added to first well at 75 uL. Serial dilutions of 1:3 were made by titrating 25:50 uL in bioassay medium across wells, leaving 50 uL per well. TSLP (at working concentration of 9 ng/ml for HuTSLP, 3 ng/ml for CyTSLP) was added at 50 uL per well to the wells containing the titrated antibody. Cells were then suspended to the appropriate density for plating at 7500 cells/50 uL per well, and added following the antibody-cytokine pre-incubation.

EC50 values are determined by non-linear regression (curve fit) of sigmoidal dose-response using GraphPad Prism 4 software. For TSLP dose response, absorbance is plotted against cytokine concentration. For neutralization activity, percentage inhibition is plotted against antibody concentration.

The assay results are shown in Table 10.

TABLE 10

Ba/F3 Cell-based Assay of Human or Cynomolgus TSLPR-Transfected Cells

| | | EC50 nM | | | | |
|---|---|---|---|---|---|---|
| TSLP | TSLPR | rat23B12 | hu23B12 | hu-cy* | cy-hu** | cy23B12 |
| hu | hu | 0.6 | 7.6 | 5.3 | 3.9 | 9.4 |
| hu | hu | 1.2 | | | | 9.0 |
| hu | hu | 0.1 | | | | 1.2 |
| hu | cyno | 0.02 | | | | 0.03 |
| hu | cyno | 0.08 | | | | 0.05 |
| cyno | cyno | 0.2 | 0.5 | 0.5 | 2.8 | 4.7 |
| cyno | cyno | 0.4 | 2.2 | 3.2 | 16 | 26, 19 |
| cyno | cyno | 0.7 | 3.0 | | | 22, 17 |

*hu-cy = humanized 23B12 VL/VH on cynomolgus constant domains
**cy-hu = cyno-ized 23B12 VL/VH on human constant domains

EXAMPLE 11

BIAcore and KinExA Affinity Measurements for Cyno-ized Anti-TSLP Antibodies

The affinity of cyno-ized anti-human TSLP 23B12 antibodies towards human and cyno TSLP ligand was determined by surface plasmon resonance using the BIAcore T100 system as described in Example 5.

The equilibrium disassociation constant for the anti-TSLP antibodies was determined using the KinExA 3000 instrument (Sapidyne Instruments Inc.). as described in Example 3.

The following materials were used:
Antibodies:
Rat anti hTSLP GNE01.23B12.H8.A4 (SPB Lot pab 330A)
Humanized anti hTSLP mAb 23B12(621HC/780LC)
Cynoized anti hTSLP mAb 23B12 (782+MAFA19/781MAFA7)
Cynoized anti hTSLP mAb 23B12 (782+hIgG1/781hukappa)
Cynoized anti hTSLP mAb 23B12 (huV-CynoC chimera)
Antigens:
Recombinant human TSLP, R&D Systems (Cat. No. 1398-TS/CF, Lot. IDK 015031)
Recombinant human TSLP, R&D Systems (Cat. No. 1398-TS, Lot. IDK 026031)
Biotinylated human TSLP (SPB Lot 38ABMA)
Other Reagents:
PMMA particles, 98 micron (Sapidyne, Cat No. 440198)
Neutravidin (Pierce, Cat No. 31000)
Cy5 conjugated Goat anti-rat IgG (H+L) (Jackson Immunoresearch Laboratories Cat. No 112-175-167, Lot 60306)
Cy5 conjugated Goat anti-huIgG (H+L) (Jackson Immunoresearch Laboratories Cat. No 109-175-088, lot 58552)
For r23B12 the following conditions were used:
Sample volume: 2 ml
Sample flow rate: 0.25 ml/min
Label volume: 1 ml
Label flow rate: 0.25 ml/min
mAb conc.: 0.05 nM
Highest Ag (TSLP) conc.: 0.5 nM
Lowest Ag (TSLP) conc.: 0.5 pM
For hu23B12 the following conditions were used:
Sample volume: 2 ml
Sample flow rate: 0.25 ml/min
Label volume: 1 ml
Label flow rate: 0.25 ml/min
mAb conc.: 0.02 nM
Highest Ag (TSLP) conc.: 0.4 nM
Lowest Ag (TSLP) conc.: 0.4 pM
For cy23B12 the following conditions were used:
Sample volume: 2 ml
Sample flow rate: 0.25 ml/min
Label volume: 1 ml
Label flow rate: 0.25 ml/min
mAb conc.: 0.1 nM
Highest Ag (TSLP) conc.: 1 nM
Lowest Ag (TSLP) conc.: 1 pM
For hu-cy23B12* and cy-hu23B12** the following conditions were used:
Sample volume: 2 ml
Sample flow rate: 0.25 ml/min
Label volume: 1 ml
Label flow rate: 0.25 ml/min mAb conc.: 0.05 nM
Highest Ag (TSLP) conc.: 1 nM
Lowest Ag (TSLP) conc.: 1 pM
For all experiments two-fold serial dilutions of the antigen were prepared and mixed with the antibody at constant concentration. The mixture was incubated for 2 hours at RT to equilibrate. The results of the BIAcore and KinExA experiments described above are summarized on Table 11.

TABLE 11

Biacore and Kinexa Binding Affinity Measurements

| TSLP | KD (pM) | | | | |
|---|---|---|---|---|---|
| | r23B12 | hu23B12 | hu-cy* | cy-hu** | cy23B12 |
| KinExA | | | | | |
| hu | 0.47 | 1.7 | 1.4 | 63 | 52 |
| BIAacore | | | | | |
| hu | 64 | 111 | 106 | 556 | 620 |
| hu | 126, 114 | | | | 1548, 2066 |
| cy | 86, 112 | 132 | 114 | 1203 | 1159, 2508 |

*hu-cy = humanized 23B12 VL/VH on cynomolgus constant domains
**cy-hu = cynoized 23B12 VL/VH on human constant domains In summary, the humanized anti-human TSLP 23B12 antibody showed approximately 5-fold reduced binding compared to the parental rat antibody based on BIAcore and KinExA measurements (Table 11). Replacing the humanized 23B12 frameworks (VLκ-III/VH-I) with those less potentially immunogenic in cynomolgus monkeys (VLκ-I/VH-III) effected a 10-fold reduction in binding compared to parental rat 23B12 and a 5-fold reduction compared to hu23B12 (Tables 10, 11).

EXAMPLE 12

Pharmacokinetic Studies of Cyno-ized Anti-TSLP 23B12 Antibodies

An ELISA assay was designed to measure the amount of cyno-ized anti-TSLP antibody reaching the plasma, serum or bronchoalveolar lavage (BAL) fluid of an animal inoculated with such an antibody.
Reagents and Buffers:
Solid Support: Nunc Maxisorp 96-Well plate (cat#439454)
Coating Buffer: 50 mM Sodium carbonate/bicarbonate pH9.6
Blocking Buffer: 0.5% BSA in PBS
Assay Diluent Buffer 0.5% BSA [wt/v], 0.05% Tween 20 [v/v], 0.25% CHAPS [wt/v], 5 mM EDTA, 0.35M NaCl in PBS (AD), pH7.4
Wash Buffer: 0.05% Tween 20 in PBS
Capturing molecule: huTSLP, 38ABM, 2497 μg/mL
Detection molecules:
 QED R799, 3600 ug/mL (a rabbit polyclonal anti-cy23B12 antibody)
 anti rabbit-HRP, JIR cat#711-036-152
Substrate: TMB (Kirkegaard & Perry, cat#50-76-03)
Stop solution: 1M H3PO4
Plate Washer SkanWasher 300 Model 12010 (Molecular Devices Cat. No. 0200-3903)
Stop solution: SpectraMax Plus 384 Microtiterplate Spectrophotometer (Molecular Devices Part No. 0112-0056
Protocol:
Coating of plates was performed as follows: huTSLP (100 ng per well) in coating buffer was incubated at 40 C overnight. Plates were washed with 1 cycle (3 washes/cycle) on a Skatron plate washer, blocked by addition of 150 μL/well blocking buffer, incubated for 60 min at room temperature on an orbital shaker and then washed for 1 cycle. The cyno-ized anti-TSLP 23B12 antibody standard was titrated across a row of eight wells (replicates) in the range of 200 ng/mL to 1.56 ng/mL using serial 2-fold dilutions. Samples are serially diluted respect to their expected levels. 100 μL of standards, controls, and samples were added to the coated plate and incubated for 120 minutes at room temperature on an orbital shaker. Plates were washed for 2 cycles and the rabbit polyclonal anti-cy23B12 antibody was added at 100 μL/well and incubated for 60 min at room temperature on an orbital shaker. Plates were washed for 2 cycles, HRP-donkey anti-rabbit IgG (H+L) (1:10,000 dilution) was added at 100 μL/well and incubated for 60 min at room temperature on an orbital shaker. Plates were washed for 2 cycles with plate rotation between cycles. TMB substrate was added at 100 μL/well and incubated approximately 5 min on an orbital shaker. Stop solution was then added at 100 μL/well and the plates read at A450-650 nm (TMB).

This assay can detect as low as 156 ng/mL of cyno-ized anti-TSLP antibodies in plasma (5% dilution) and serum; and as low as 3.2 ng/mL in BAL fluid.

This ELISA assay was used to measure the pharmacokinetics of cyno-ized anti-TSLP 23B12 antibodies after administration to mice and monkeys.

A single dose PK study was conducted in normal CD-1 mice. In this study, ten mice received 10 mg/kg of the antibody by intravenous (IV) administration; and ten mice received 10 mg/kg of the antibody by subcutaneous (SC) administration. The results of the study are summarized in Table 12.

TABLE 12

| Route | Clearance (mL/day/kg) | Vss (mL/kg) | AUC 0-last (μg*day/mL) | t½ terminal (day) | Tmax (day) | Cmax (μg/mL) | F (%) |
|---|---|---|---|---|---|---|---|
| IV | 24.8 | 220 | 366 | 6.69 | — | — | — |
| IV (w/o Day 10) | 22.8 | 198 | 404 | 6.36 | | | |
| SC | — | — | 370 | 3.13 | 0.667 | 73.7 | 95.6 |

Table 13 summarizes the percentage of cyno-ized anti-TSLP antibody found in the BAL fluid versus in the serum at various time points after IV or SC administration.

TABLE 13

| Time point (day) | IV BAL/Serum Mean (%) | SC BAL/Serum Mean (%) |
|---|---|---|
| 0.250 | 1.686 | 4.080 |
| 1.000 | 2.811 | 5.880 |
| 3.000 | 5.677 | 7.301 |
| 7.000 | 13.740 | 16.945 |
| 10.000 | 14.319 | 5.064 |
| 14.000 | 6.517 | 16.912 |

Two single dose PK studies were also conducted in cynomolgus monkeys. The two studies used different formulations of the cyno-ized anti-TSLP 23B12 antibody: one containing 0.05% of Triton X-100 and one without Triton X-100. Each study contained three monkeys. The dose used in each study is indicated in Table 14. The antibody was administered subcutaneously. The results of the studies are summarized in Tables 14 and 15.

TABLE 14

| Formulation | Animal ID | Dose (mg/kg) | CL/F (mL/day/kg) | AUC 0-last (mg*day/mL) | t½ terminal (day) | Tmax (day) | Cmax (mg/mL) |
|---|---|---|---|---|---|---|---|
| no Triton | Cyno M2-04 | 5.6 | 15.1 | 326 (600) | 9.18 | 1 | 26.4 |
| | Cyno M7-05 | 5.6 | 7.96 | 594 (1090) | 10 | 1 | 48.3 |
| | Cyno M21-05 | 5.7 | 8.82 | 491 (887) | 12.4 | 2 | 34 |
| 0.05% Triton X100 | Cyno 2172 | 10.7 | 10.3 | 666 | 8.15 | 4 | 61.6 |
| | Cyno 3048 | 10.3 | 8.27 | 778 | 8.86 | 2 | 88.8 |
| | Cyno 5102 | 9.8 | 8.14 | 753 | 9.08 | 1 | 89.9 |

TABLE 15

| Formulation | | BAL/Serum Ratio (%) | | | |
|---|---|---|---|---|---|
| No Triton | Time point (day) | M2-04 | M7-05 | M21-05 | Mean |
| | 3 | 0.657 | 0.712 | 0.335 | 0.568 |
| | 10 | 1.83 | 1.15 | 1.81 | 1.60 |
| +0.05% Triton X100 | Time point (day) | 2172 | 3048 | 5102 | Mean |
| | 3 | 0.313 | 0.492 | 1.39 | 0.733 |
| | 10 | 0.090 | 0.620 | 0.693 | 0.467 |

EXAMPLE 13

Administration of Cyno-ized Anti-TSLP 23B12 Antibodies to Cynomolgus Monkeys

Cyno-ized anti-TSLP 23B12 antibodies were produced from a stably transfected CHO cell line in suspension culture. The supernantant was harvested, contreated, and purified using several standard chromatogrphic steps to achieve a low endotoxin, >95% pure preparation. The purified antibody was formulated for stability during handling and use, including multiple freeze-thaws, in 20 mM sodium acetate, pH 5.5, 7% (w/v) sucrose, and 0.05% Triton X-100. This antibody is to be administered to house dust mite (HDM) allergic cynomolgus monkeys to demonstrate the effectiveness of an anti-TSLP antibodies to treat allergic lung inflammation. This animal model will make possible the collection of airway tissues, BAL fluid, and associated PBMC's harvested from the control and cy23B12 treated animals; and will provide the ability to access efficacy in Early Allergic Reactions (EAR) and Late Allergic Reactions (LAR). Further information regarding non-primate models of chronic allergic asthma are well known in the art. See, e.g., Schelegle et al., *Am. J. Pathology* 158(1):333-341 (2001); Avdalovic et al., *Am. J. Respir. Crit. Care Med.* 174:1069-74 (2006) Care and Van Scott et al., *J. Appl. Physiol.* 99(6):2080-2086 (2005).

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

Citation of the above publications or documents is not intended as an admission that any of the foregoing is pertinent prior art, nor does it constitute any admission as to the contents or date of these publications or documents. U.S. patents and other publications referenced herein are hereby incorporated by reference.

What is claimed is:

1. An isolated nucleic acid molecule encoding a heavy chain variable region of an antibody or an antigen binding fragment thereof that binds to human and cyno TSLP, wherein the antibody or the fragment comprises a heavy chain variable region comprising the three CDR sequences set forth in SEQ ID NOs: 1, 2 and 3 and a light chain variable region comprising the three CDR sequences set forth in SEQ ID NOs: 4, 5 and 6.

2. An isolated nucleic acid molecule encoding a light chain variable region of an antibody or an antigen binding fragment thereof that binds to human and cyno TSLP, wherein the antibody or the fragment comprises a heavy chain variable region comprising the three CDR sequences set forth in SEQ ID NOs: 1, 2 and 3 and a light chain variable region comprising the three CDR sequences set forth in SEQ ID NOs: 4, 5 and 6.

3. An isolated expression vector comprising at least one of the nucleic acids selected from claim 1 or 2 operably linked to control sequences that are recognized by a host cell when the host cell is transfected with the vector.

4. An isolated host cell comprising the expression vector of claim 3.

5. The isolated nucleic acid molecule according to claim 1, wherein the nucleic acid molecule comprises the sequence set forth in SEQ ID NO: 9.

6. The isolated nucleic acid molecule according to claim 2, wherein the nucleic acid molecule comprises the sequence set forth in SEQ ID NO: 11.

* * * * *

```
SEQUENCE LISTING

<160> NUMBER OF SEQ ID NOS: 18

<210> SEQ ID NO 1
<211> LENGTH: 10
<212> TYPE: PRT
<213> ORGANISM: Rattus norvegicus

<400> SEQUENCE: 1

Gly Tyr Ile Phe Thr Asp Tyr Ala Met His
1               5                   10

<210> SEQ ID NO 2
<211> LENGTH: 17
<212> TYPE: PRT
<213> ORGANISM: Rattus norvegicus

<400> SEQUENCE: 2

Thr Phe Ile Pro Leu Leu Asp Thr Ser Asp Tyr Asn Gln Asn Phe Lys
1               5                   10                  15

Gly

<210> SEQ ID NO 3
<211> LENGTH: 11
<212> TYPE: PRT
<213> ORGANISM: Rattus norvegicus
```

<400> SEQUENCE: 3

Met Gly Val Thr His Ser Tyr Val Met Asp Ala
1               5                   10

<210> SEQ ID NO 4
<211> LENGTH: 11
<212> TYPE: PRT
<213> ORGANISM: Rattus norvegicus

<400> SEQUENCE: 4

Arg Ala Ser Gln Pro Ile Ser Ile Ser Val His
1               5                   10

<210> SEQ ID NO 5
<211> LENGTH: 7
<212> TYPE: PRT
<213> ORGANISM: Rattus norvegicus

<400> SEQUENCE: 5

Phe Ala Ser Gln Ser Ile Ser
1               5

<210> SEQ ID NO 6
<211> LENGTH: 9
<212> TYPE: PRT
<213> ORGANISM: Rattus norvegicus

<400> SEQUENCE: 6

Gln Gln Thr Phe Ser Leu Pro Tyr Thr
1               5

<210> SEQ ID NO 7
<211> LENGTH: 120
<212> TYPE: PRT
<213> ORGANISM: Rattus norvegicus

<400> SEQUENCE: 7

Glu Glu Lys Leu Gln Gln Ser Gly Asp Asp Leu Val Arg Pro Gly Ala
1               5                   10                  15

Ala Val Lys Met Ser Cys Lys Ala Ser Gly Tyr Ile Phe Thr Asp Tyr
                20                  25                  30

Ala Met His Trp Val Lys Gln Arg Pro Gly Gln Gly Leu Glu Trp Ile
            35                  40                  45

Gly Thr Phe Ile Pro Leu Leu Asp Thr Ser Asp Tyr Asn Gln Asn Phe
        50                  55                  60

Lys Gly Arg Ala Thr Leu Thr Ala Asp Lys Ser Ser Asn Thr Ala Tyr
65                  70                  75                  80

Met Glu Leu Ser Arg Leu Thr Ser Glu Asp Ser Ala Val Tyr Tyr Cys
                85                  90                  95

Ala Arg Met Gly Val Thr His Ser Tyr Val Met Asp Ala Trp Gly Gln
                100                 105                 110

Gly Ala Ser Val Thr Val Ser Ser
            115                 120

<210> SEQ ID NO 8
<211> LENGTH: 108
<212> TYPE: PRT
<213> ORGANISM: Rattus norvegicus

<400> SEQUENCE: 8

Asp Ile Val Leu Thr Gln Ser Pro Ala Thr Leu Ser Val Thr Pro Gly

```
1               5                  10                 15
Glu Ser Val Ser Leu Ser Cys Arg Ala Ser Gln Pro Ile Ser Ile Ser
                20                 25                 30

Val His Trp Phe Gln Gln Lys Ser Asn Glu Ser Pro Arg Leu Leu Ile
        35                 40                 45

Lys Phe Ala Ser Gln Ser Ile Ser Gly Ile Pro Ser Arg Phe Ser Gly
    50                 55                 60

Ser Gly Ser Gly Thr Asp Phe Thr Leu Asn Ile Asn Arg Val Glu Ser
65                 70                 75                 80

Glu Asp Phe Ser Val Tyr Tyr Cys Gln Gln Thr Phe Ser Leu Pro Tyr
                85                 90                 95

Thr Phe Gly Thr Gly Thr Lys Leu Glu Leu Lys Arg
            100                105

<210> SEQ ID NO 9
<211> LENGTH: 360
<212> TYPE: DNA
<213> ORGANISM: Artificial
<220> FEATURE:
<223> OTHER INFORMATION: Humanized antibody sequence

<400> SEQUENCE: 9
caggtgcagc tggtgcagtc tggcgctgag gtgaagaagc ctggcgcctc cgtgaaggtc    60
tcctgcaagg cttctggcta catcttcacc gactacgcca tgcactgggt gcggcaggcc   120
cctggccagg gctggagtg gatgggtacc ttcatccctc tgctggacac cagcgactac   180
aaccagaact tcaagggcag agtcaccatg accacagaca tccaccag cacagcctac     240 atggagctga ggagcctgag atctgacgac accgccgtgt attactgtgc cagaatggga   300
gtgacccaca gctacgtgat ggatgcatgg ggccagggca ccctggtcac cgtctccagc   360

<210> SEQ ID NO 10
<211> LENGTH: 120
<212> TYPE: PRT
<213> ORGANISM: Artificial
<220> FEATURE:
<223> OTHER INFORMATION: Humanized antibody sequence

<400> SEQUENCE: 10

Gln Val Gln Leu Val Gln Ser Gly Ala Glu Val Lys Lys Pro Gly Ala
1               5                  10                 15

Ser Val Lys Val Ser Cys Lys Ala Ser Gly Tyr Ile Phe Thr Asp Tyr
                20                 25                 30

Ala Met His Trp Val Arg Gln Ala Pro Gly Gln Gly Leu Glu Trp Met
        35                 40                 45

Gly Thr Phe Ile Pro Leu Leu Asp Thr Ser Asp Tyr Asn Gln Asn Phe
    50                 55                 60

Lys Gly Arg Val Thr Met Thr Thr Asp Thr Ser Thr Ser Thr Ala Tyr
65                 70                 75                 80

Met Glu Leu Arg Ser Leu Arg Ser Asp Asp Thr Ala Val Tyr Tyr Cys
                85                 90                 95

Ala Arg Met Gly Val Thr His Ser Tyr Val Met Asp Ala Trp Gly Gln
            100                105                110

Gly Thr Leu Val Thr Val Ser Ser
            115                120

<210> SEQ ID NO 11
<211> LENGTH: 324
<212> TYPE: DNA
```

<213> ORGANISM: Artificial
<220> FEATURE:
<223> OTHER INFORMATION: Humanized antibody sequence

<400> SEQUENCE: 11

```
gaaattgtgc tgactcagag cccaggcacc ctgtctctgt ctccaggcga gagagccacc    60
ctctcctgcc gggccagcca gcccatctcc atcagcgtgc actggtacca gcagaaacca   120
ggacaggctc caaggctgct gatctacttt gcctcccaga gcatctccgg gatccccgat   180
aggttcagcg gatccggatc tgggacagat ttcaccctca ccatcagcag actggagcct   240
gaagatttcg cagtgtatta ctgtcagcag accttcagcc tgccttacac tttcggccaa   300
gggaccaagg tggagatcaa gcgt                                          324
```

<210> SEQ ID NO 12
<211> LENGTH: 108
<212> TYPE: PRT
<213> ORGANISM: Artificial
<220> FEATURE:
<223> OTHER INFORMATION: Humanized antibody sequence

<400> SEQUENCE: 12

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Pro Ile Ser Ile Ser
            20                  25                  30
Val His Trp Tyr Gln Gln Lys Pro Gly Gln Ala Pro Arg Leu Leu Ile
        35                  40                  45
Tyr Phe Ala Ser Gln Ser Ile Ser Gly Ile Pro Asp Arg Phe Ser Gly
    50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys Gln Gln Thr Phe Ser Leu Pro Tyr
                85                  90                  95
Thr Phe Gly Gln Gly Thr Lys Val Glu Ile Lys Arg
            100                 105
```

<210> SEQ ID NO 13
<211> LENGTH: 1350
<212> TYPE: DNA
<213> ORGANISM: Artificial
<220> FEATURE:
<223> OTHER INFORMATION: Humanized antibody sequence

<400> SEQUENCE: 13

```
caggtgcagc tggtgcagtc tggcgctgag gtgaagaagc ctggcgcctc cgtgaaggtc    60
tcctgcaagg cttctggcta catcttcacc gactacgcca tgcactgggt gcggcaggcc   120
cctggccagg gctggagtg atgggtacc ttcatccctc tgctggacac cagcgactac   180
aaccagaact tcaagggcag agtcaccatg accacagaca tccaccagac acagcctac   240
atggagctga ggagcctgag atctgacgac accgccgtgt attactgtgc cagaatggga   300
gtgacccaca gctacgtgat ggatgcatgg ggccagggca cctggtcac cgtctccagc   360
gctagcacca aggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
```

-continued

```
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                   1350
```

<210> SEQ ID NO 14
<211> LENGTH: 450
<212> TYPE: PRT
<213> ORGANISM: Artificial
<220> FEATURE:
<223> OTHER INFORMATION: Humanized antibody sequence

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Ala Met His Trp Val Arg Gln Ala Pro Gly Gln Gly Leu Glu Trp Met
        35                  40                  45

Gly Thr Phe Ile Pro Leu Leu Asp Thr Ser Asp Tyr Asn Gln Asn Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Met Gly Val Thr His Ser Tyr Val Met Asp Ala Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 15
<211> LENGTH: 642
<212> TYPE: DNA
<213> ORGANISM: Artificial
<220> FEATURE:
<223> OTHER INFORMATION: Humanized antibody sequence

<400> SEQUENCE: 15
gaaattgtgc tgactcagag cccaggcacc ctgtctctgt ctccaggcga gagagccacc      60
ctctcctgcc gggccagcca gcccatctcc atcagcgtgc actggtacca gcagaaacca     120
ggacaggctc caaggctgct gatctacttt gcctcccaga gcatctccgg gatcccccgat    180 aggttcagcg gatccggatc tgggacagat tcaccctca ccatcagcag actggagcct     240
gaagatttcg cagtgtatta ctgtcagcag accttcagcc tgcctacac tttcggccaa     300 gggaccaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 16
<211> LENGTH: 214
<212> TYPE: PRT
<213> ORGANISM: Artificial
<220> FEATURE:
```

<223> OTHER INFORMATION: Humanized antibody sequence

<400> SEQUENCE: 16

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Pro Ile Ser Ile Ser
            20                  25                  30

Val His Trp Tyr Gln Gln Lys Pro Gly Gln Ala Pro Arg Leu Leu Ile
        35                  40                  45

Tyr Phe Ala Ser Gln Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Thr Phe Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 17
<211> LENGTH: 233
<212> TYPE: PRT
<213> ORGANISM: Artificial
<220> FEATURE:
<223> OTHER INFORMATION: Cyonized antibody sequence with signal peptide

<400> SEQUENCE: 17

```
Met Ala Pro Val Gln Leu Leu Gly Leu Leu Val Leu Phe Leu Pro Ala
1               5                   10                  15

Met Arg Cys Asp Ile Gln Met Thr Gln Ser Pro Ser Ser Leu Ser Ala
            20                  25                  30

Ser Val Gly Asp Arg Val Thr Ile Thr Cys Arg Ala Ser Gln Pro Ile
        35                  40                  45

Ser Ile Ser Val His Trp Tyr Gln Gln Lys Pro Gly Lys Ala Pro Lys
    50                  55                  60

Leu Leu Ile Tyr Phe Ala Ser Gln Ser Ile Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Thr Phe Ser
            100                 105                 110

Leu Pro Tyr Thr Phe Gly Gln Gly Thr Lys Val Glu Ile Lys Arg Thr
        115                 120                 125
```

```
Val Ala Ala Pro Ser Val Phe Ile Phe Pro Ser Glu Asp Gln Val
            130                 135                 140

Lys Ser Gly Thr Val Ser Val Val Cys Leu Leu Asn Asn Phe Tyr Pro
145                 150                 155                 160

Arg Glu Ala Ser Val Lys Trp Lys Val Asp Gly Val Leu Lys Thr Gly
                165                 170                 175

Asn Ser Gln Glu Ser Val Thr Glu Gln Asp Ser Lys Asp Asn Thr Tyr
            180                 185                 190

Ser Leu Ser Ser Thr Leu Thr Leu Ser Ser Thr Asp Tyr Gln Ser His
        195                 200                 205

Asn Val Tyr Ala Cys Glu Val Thr His Gln Gly Leu Ser Ser Pro Val
        210                 215                 220

Thr Lys Ser Phe Asn Arg Gly Glu Cys
225                 230
```

<210> SEQ ID NO 18
<211> LENGTH: 472
<212> TYPE: PRT
<213> ORGANISM: Artificial
<220> FEATURE:
<223> OTHER INFORMATION: Cyonized antibody sequence with signal peptide

<400> SEQUENCE: 18

```
Met Ala Val Leu Gly Leu Leu Phe Cys Leu Val Thr Phe Pro Ser Cys
1               5                   10                  15

Val Leu Ser Gln Val Gln Leu Val Glu Ser Gly Gly Gly Val Val Gln
            20                  25                  30

Pro Gly Arg Ser Leu Arg Leu Ser Cys Ala Ala Ser Gly Tyr Ile Phe
        35                  40                  45

Thr Asp Tyr Ala Met His Trp Val Arg Gln Ala Pro Gly Lys Gly Leu
    50                  55                  60

Glu Trp Val Ala Thr Phe Ile Pro Leu Leu Asp Thr Ser Asp Tyr Asn
65                  70                  75                  80

Gln Asn Phe Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Met Gly Val Thr His Ser Tyr Val Met Asp Ala
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ser Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Val Cys Asn Val
    210                 215                 220

Asn His Lys Pro Ser Asn Thr Lys Val Asp Lys Arg Val Glu Ile Lys
225                 230                 235                 240

Thr Cys Gly Gly Gly Ser Lys Pro Pro Thr Cys Pro Pro Cys Pro Ala
                245                 250                 255

Pro Glu Leu Leu Gly Gly Pro Ser Val Phe Leu Phe Pro Pro Lys Pro
```

-continued

```
            260                 265                 270
Lys Asp Thr Leu Met Ile Ser Arg Thr Pro Glu Val Thr Cys Val Val
        275                 280                 285

Val Asp Val Ser Gln Glu Asp Pro Asp Val Lys Phe Asn Trp Tyr Val
        290                 295                 300

Asn Gly Ala Glu Val His His Ala Gln Thr Lys Pro Arg Glu Thr Gln
305                 310                 315                 320

Tyr Asn Ser Thr Tyr Arg Val Val Ser Val Leu Thr Val Thr His Gln
                325                 330                 335

Asp Trp Leu Asn Gly Lys Glu Tyr Thr Cys Lys Val Ser Asn Lys Ala
            340                 345                 350

Leu Pro Ala Pro Ile Gln Lys Thr Ile Ser Lys Asp Lys Gly Gln Pro
        355                 360                 365

Arg Glu Pro Gln Val Tyr Thr Leu Pro Pro Ser Arg Glu Glu Leu Thr
    370                 375                 380

Lys Asn Gln Val Ser Leu Thr Cys Leu Val Lys Gly Phe Tyr Pro Ser
385                 390                 395                 400

Asp Ile Val Val Glu Trp Glu Ser Ser Gly Gln Pro Glu Asn Thr Tyr
                405                 410                 415

Lys Thr Thr Pro Pro Val Leu Asp Ser Asp Gly Ser Tyr Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```